United States Patent
Kuniyasu et al.

(10) Patent No.: US 7,199,509 B2
(45) Date of Patent: Apr. 3, 2007

(54) MULTILAYERED STRUCTURE AND METHOD OF MANUFACTURING THE SAME, AND ULTRASONIC TRANSDUCER

(75) Inventors: Toshiaki Kuniyasu, Kaisei-machi (JP); Hiroshi Maeda, Minami-Ashigara (JP); Kazuhiro Nishida, Minami-Ashigara (JP); Takayuki Fujiwara, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 118 days.

(21) Appl. No.: 11/030,069

(22) Filed: Jan. 7, 2005

(65) Prior Publication Data

US 2006/0154075 A1    Jul. 13, 2006

(30) Foreign Application Priority Data

Jan. 9, 2004    (JP)    ............................. 2004-003946

(51) Int. Cl.
*H01L 41/047*    (2006.01)
(52) U.S. Cl. .................... 310/365; 310/364; 29/25.35; 29/594
(58) Field of Classification Search ................ 310/328, 310/364–366; 29/25.35, 594
See application file for complete search history.

(56) References Cited

U.S. PATENT DOCUMENTS 4,845,399 A * 7/1989 Yasuda et al. .............. 310/366
6,114,798 A * 9/2000 Maruyama et al. ......... 310/365
6,757,947 B2 * 7/2004 Seipler et al. ............. 29/25.35

FOREIGN PATENT DOCUMENTS

JP    6-291380 A    10/1994

* cited by examiner

*Primary Examiner*—Tom Dougherty
*Assistant Examiner*—J. Aguirrechea
(74) *Attorney, Agent, or Firm*—Sughrue Mion, PLLC

(57) ABSTRACT

A multilayered structure which includes insulating layers and electrode layers and can be easily arrayed. The multilayered structure is manufactured by using a substrate on which first and second groups of columnar structures are arranged in a predetermined arrangement, and includes: a first electrode layer formed by forming a film of a conducting material on the substrate or an insulating layer except for portions around the first group of columnar structures; an insulating layer formed by spraying powder of an insulating material on the first electrode layer to deposit the powder thereon; a second electrode layer formed by forming a film of a conducting material on the insulating layer except for portions around the second group of columnar structures; and interconnections formed by filing, with a conducting material, holes formed by removing the columnar structures from the substrate.

10 Claims, 23 Drawing Sheets

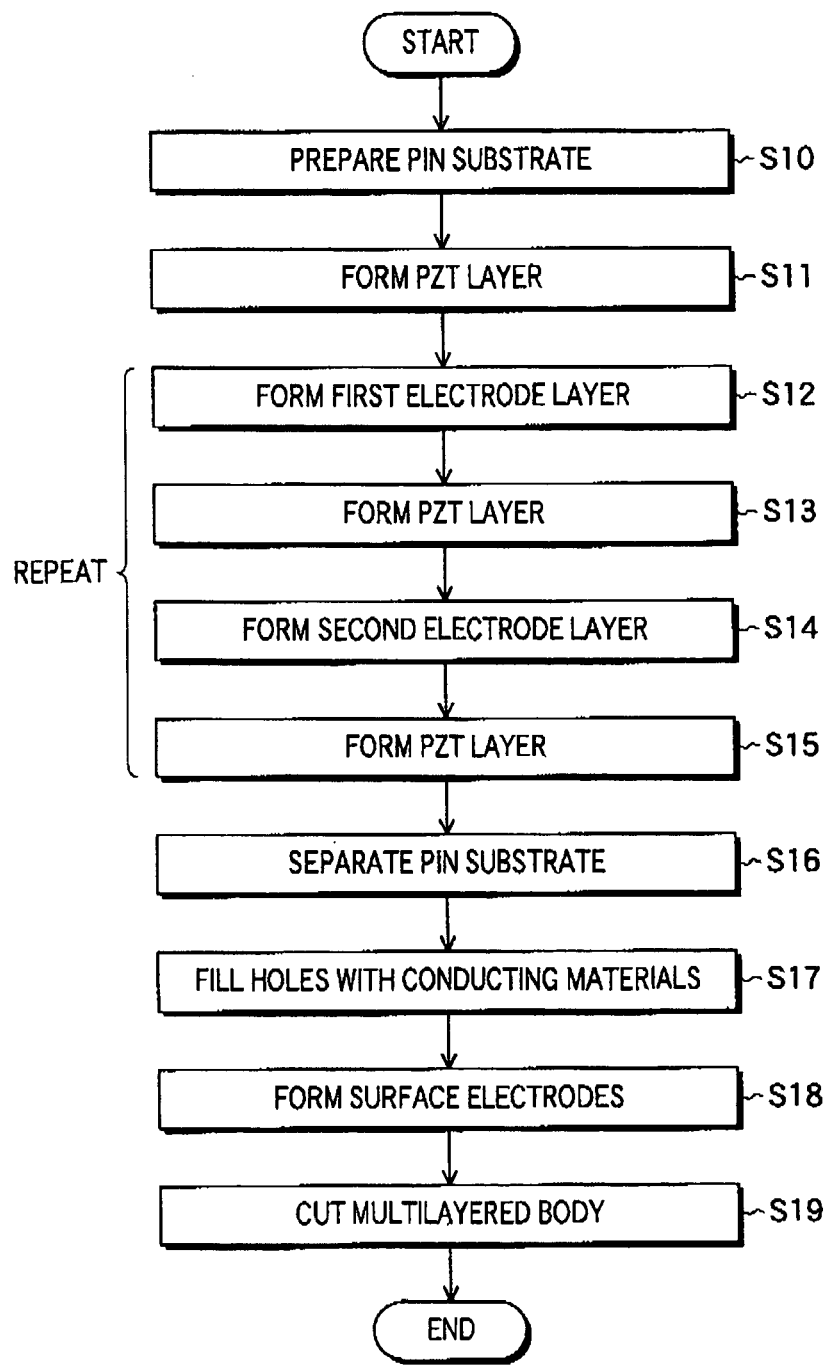

70

74

CONDUCTING MATERIAL

⇧
CONDUCTING MATERIAL

PZT POWDER

CONDUCTING MATERIAL

ULTRASONIC WAVE

TO MAIN BODY

MULTILAYERED STRUCTURE AND METHOD OF MANUFACTURING THE SAME, AND ULTRASONIC TRANSDUCER

BACKGROUND OF THE INVENTION

1. Field of the Invention

The present invention relates to a multilayered structure in which insulating material layers and electrode layers are alternately stacked and a method of manufacturing the same. Further, the present invention relates to an ultrasonic transducer including such a multilayered structure and to be used for transmitting and receiving ultrasonic waves in ultrasonic diagnosis and nondestructive inspection.

2. Description of a Related Art

Multilayered structures, in each of which insulating material (dielectric material) layers and electrode layers are alternately formed, are utilized not only for multilayered capacitors but also in various uses such as piezoelectric pumps, piezoelectric actuators, ultrasonic transducers and so on. In recent years, with the developments of MEMS (micro electromechanical systems) related devices, elements each having such a multilayered structure have been microfabricated still further and packaged more densely.

In microfabrication of an element having opposed electrodes, since the smaller the area of the element is made, the smaller the capacity between the electrodes becomes, a problem occurs that the electrical impedance of the element rises. For example, when the electrical impedance rises in a piezoelectric actuator, the impedance matching can not be taken with a signal circuit for driving the piezoelectric actuator and power becomes difficult to be supplied, and thereby, the performance as the piezoelectric actuator is degraded. Alternatively, in an ultrasonic transducer employing a piezoelectric element, detection sensitivity of ultrasonic waves is dropped. Accordingly, in order to enlarge the capacity between electrodes while microfabricating the element, plural piezoelectric material layers and plural electrode layers are alternatively stacked. That is, the capacity between electrodes of the entire element can be made larger by connecting the stacked plural layers in parallel.

FIGS. 23A and 23B are sectional views showing a conventional multilayered structure (piezoelectric device) in which plural piezoelectric material layers and plural electrode layers are stacked. As shown in FIGS. 23A and 23B, in order to connect in parallel the plural electrode layers that sandwich plural piezoelectric material layers 100, interconnection is performed from side surfaces of the multilayered structure.

In the multilayered structure as shown in FIG. 23A, electrodes 101 are formed so that one ends thereof may extend to one wall surface of the multilayered structure, and electrodes 102 are formed so that one ends thereof may extend to the other wall surface of the multilayered structure. Thereby, the electrodes 101 are connected to a side interconnection 103 formed on the one side surface and insulated from a side interconnection 104 formed on the other side surface. Contrary, the electrodes 102 are connected to the side interconnection 104 and insulated from the side interconnection 103. By applying a voltage difference between the side interconnection 103 and the side interconnection 104, an electric field is applied to each of the piezoelectric material layers 100 respectively disposed between the electrodes 101 and the electrodes 102, and the piezoelectric material layers 100 expand and contract by the piezoelectric effect.

By the way, as shown in FIG. 23A, in each layer of the electrodes 101 and 102, insulating regions 105 in which no electrode is formed are provided for insulating the electrodes from either of the side interconnections. The insulating regions 105 do not expand or contract even when a voltage is applied to the multilayered structure 100. On this account, stress is concentrated on this part and this part is easy to break, and therefore, a problem occurs that the reliability of the product becomes low.

In order to prevent such a breakage due to stress concentration, a multilayered structure as shown in FIG. 23B has been proposed. In this multilayered structure, electrodes 111 and 112 are formed over the entire surfaces of the piezoelectric material layers 100. Further, one ends of the electrodes 111 and 112 exposed on the side surfaces of the multilayered structure are covered by insulating materials 115. Thereby, the electrodes 111 are connected to a side interconnection 113 and insulated from a side interconnection 114. Contrary, the electrodes 112 are connected to the side interconnection 114 and insulated from the side interconnection 113.

However, in the multilayered structure as shown in FIG. 23B, since the insulating regions 115 and side interconnections 113 and 114 are formed on the side surfaces, it is difficult to fabricate an arrayed multilayered structure in which a large number of multilayered structures are densely arranged.

By the way, Japanese Patent Application Publication JP-A-6-291380 discloses that a multilayered body is obtained by forming multilayered structure of internal electrode layers and dielectric material layers, and external electrodes by repeating injection deposition of ultrafine particles of internal electrode material, dielectric material and external electrode material by using plural nozzles having different output end forms in a certain order (the fourth page, FIG. 4). By such a fabrication method, a multilayered ceramic dielectric material can be obtained without employing an organic material such as a binder.

The injection deposition method is a film forming method of depositing a raw material by spraying the fine particles of the raw material toward a substrate, and also referred to as "aerosol deposition (AD) method" or "gas deposition method". In the injection deposition method, the fine particles of the raw material are sprayed at high speed on an under layer such as the substrate or a deposit that has been previously formed, and thereby, a phenomenon called "anchoring" occurs in which the fine particles of the raw material cut into the under layer. At the time of the impingement, a strong film is formed by the mechanochemical reaction in which the fine particles of the raw material are crushed and the crushed faces adhere to the under layer.

In the multilayered structure as shown in FIG. 4 of JP-A-6-291380, not only a lower electrode 2, piezoelectric materials 3 and an upper electrode 4, but also external electrodes 5a and 5b as side interconnections are formed by the injection deposition method. The external electrodes 5a and 5b are required to have thicknesses equal to that of the piezoelectric material in order to connect predetermined interconnections, which are located between the plural piezoelectric materials 3, to each other. However, because nickel (Ni) or palladium silver (Ag—Pd) as a material of the side interconnections 5a and 5b is softer compared to a platinum (Pt) and titanium (Ti) as a material of the lower electrode 2, when the side interconnections are formed by the injection deposition method, anchoring occurs but mechanochemical reaction hardly occurs. On this account, there is a possibility that strong side interconnections cannot be formed. Contrary, it is conceivable that, at this time, ablation (corrosion) occurs and the film deposited once is separated. Further, when the fine particles of the raw material are sprayed from the nozzle, a beam of aerosol (gas in which raw material powder is floating) broadens, and therefore, the edges of the piezoelectric materials become tapered. Accordingly, the repeated formation of multilayers makes the widths of the piezoelectric material layers narrower, and thereby, it is difficult to fabricate an ideal column piezoelectric material. Furthermore, in the case where electrodes are located on the side surfaces of the piezoelectric materials, it becomes difficult to package a large number of microstructures with high density.

SUMMARY OF THE INVENTION

The present invention has been achieved in view of the above-described problems. An object of the present invention is to provide a multilayered structure, which includes insulating layers and plural electrode layers and can be easily arrayed, and a method of manufacturing such a multilayered structure. Another object of the present invention is to provide an ultrasonic transducer employing such a multilayered structure.

In order to solve the above-described problems, a method of manufacturing a multilayered structure according to the present invention comprises the steps of: arranging a plurality of columnar structures including a first group of columnar structures and a second group of columnar structures on a substrate in a predetermined arrangement; forming a first electrode layer by forming a film of a conducting material on the substrate or an insulating layer formed over the substrate except for portions around the first group of columnar structures; forming an insulating layer by spraying powder of an insulating material on the first electrode layer formed over the substrate to deposit the powder thereon; and forming a second electrode layer by forming a film of a conducting material on the insulating layer except for portions around the second group of columnar structures.

A multilayered structure according to a first aspect of the present invention is a multilayered structure manufactured by using a substrate on which a plurality of columnar structures including a first group of columnar structures and a second group of columnar structures are arranged in a predetermined arrangement, and the multilayered structure comprises: a first electrode layer formed by forming a film of a conducting material on the substrate or an insulating layer formed over the substrate except for portions around the first group of columnar structures; an insulating layer formed by spraying powder of an insulating material on the first electrode layer formed over the substrate to deposit the powder thereon; a second electrode layer formed by forming a film of a conducting material on the insulating layer except for portions around the second group of columnar structures; and a plurality of interconnections formed by filing, with a conducting material, a plurality of holes formed by removing the plurality of columnar structures from the substrate on which at least the first electrode layer, the insulating layer and the second electrode layer are formed.

A multilayered structure according to a second aspect of the present invention is a multilayered structure manufactured by using a substrate, and the multilayered structure comprises: a plurality of electrodes formed by arranging a plurality of columnar structures including a first group of columnar structures and a second group of columnar structures formed of a conducting material on the substrate in a predetermined arrangement; a first electrode layer formed by forming a film of a conducting material on the substrate or an insulating layer formed over the substrate except for portions around the first group of columnar structures; an insulating layer formed by spraying powder of an insulating material on the first electrode layer formed over the substrate to deposit the powder thereon; and a second electrode layer formed by forming a film of a conducting material on the insulating layer except for portions around the second group of columnar structures.

An ultrasonic transducer according to the first aspect of the present invention is an ultrasonic transducer manufactured by using a substrate on which a plurality of columnar structures including a first group of columnar structures and a second group of columnar structures are arranged in a predetermined arrangement, and the ultrasonic transducer comprises: the substrate to be used as an acoustic matching layer; a first electrode layer formed by forming a film of a conducting material on the substrate except for portions around the first group of columnar structures; a piezoelectric material layer formed by spraying powder of a piezoelectric material on the first electrode layer formed over the substrate to deposit the powder thereon; a second electrode layer formed by forming a film of a conducting material on the piezoelectric material layer except for portions around the second group of columnar structures; and a plurality of interconnections formed by filing, with a conducting material, a plurality of holes formed by removing the plurality of columnar structures from the substrate on which at least the first electrode layer, the piezoelectric material layer and the second electrode layer are formed.

Further, an ultrasonic transducer according to the second aspect of the present invention comprises: a substrate, on which a plurality of columnar structures including a first group of columnar structures and a second group of columnar structures are arranged in a predetermined arrangement, to be used as an acoustic matching layer; a first electrode layer formed by forming a film of a conducting material on the substrate except for portions around the first group of columnar structures; a piezoelectric material layer formed by spraying powder of a piezoelectric material on the first electrode layer formed over the substrate to deposit the powder thereon; and a second electrode layer formed by forming a film of a conducting material on the piezoelectric material layer except for portions around the second group of columnar structures.

According to the present invention, arraying of the multilayered structures, which has been conventionally difficult, can be realized with high reliability.

BRIEF DESCRIPTION OF THE DRAWINGS

FIG. 3 is a flowchart showing a method of manufacturing a multilayered structure according to the first embodiment of the present invention;

DESCRIPTION OF THE PREFERRED EMBODIMENTS

Figure 1A:
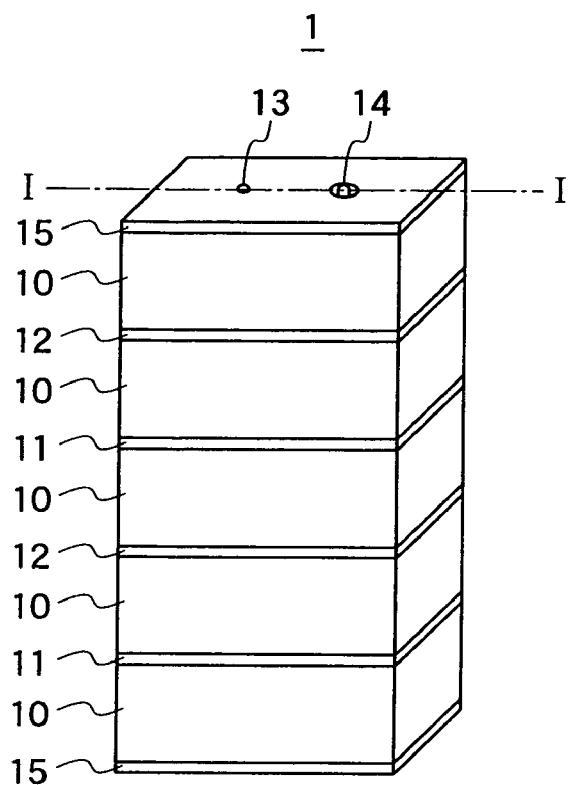
FIG. 1A is an overview diagram showing a multilayered structure according to the first embodiment of the present invention.

Hereinafter, preferred embodiments of the present invention will be described in detail by referring to the drawings. The same component elements are assigned with the same reference numerals and the description thereof will be omitted.

Figure 1B:
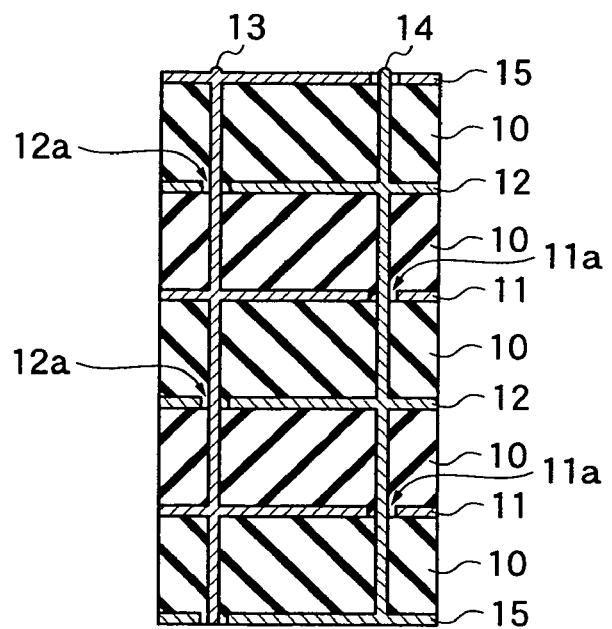
FIG. 1B is a sectional view along I—I plane in FIG. 1A.

FIG. 1A is an overview diagram showing a multilayered structure according to the first embodiment of the present invention, and FIG. 1B is a sectional view along I—I plane in FIG. 1A. As shown in FIG. 1A, a multilayered structure 1 is a micro columnar structure having a bottom surface with sides of about 0.3 mm to about 1.0 mm and a height of about 1.0 mm. The multilayered structure 1 includes plural PZT (Pb(lead) zirconate titanate) layers 10, plural first electrode layers 11, plural second electrode layers 12, vertical interconnections 13 and 14, and surface electrodes 15.

As shown in FIG. 1A and 1B, the PZT layers 10 are located between the first electrode layers 11 and the second electrode layers 12, respectively. By applying a voltage between the first electrode layers 11 and the second electrode layers 12, the PZT layers 10 expand and contract by the piezoelectric effect. Thus, the multilayered structure employing the piezoelectric material such as PZT in insulating layers (dielectricmaterial layers) is used for piezoelectric pumps, piezoelectric actuators, ultrasonic transducers for transmitting and receiving ultrasonic waves in an ultrasonic probe, and so on. Further, in the structure having such a multilayered structure, areas of the opposed electrodes can be increased compared to a single layer structure, and thereby, electric impedance can be made lower. Therefore, compared to the single layer structure, the multilayered structure operates more efficiently for the applied voltage.

As shown in FIG. 1B, at least one insulating region 11a is provided within a surface of each first electrode layer 11. In this application, the insulating region 11a refers to a region in which a conducting material is removed in the first electrode layer 11. Similarly, at least one insulating region 12a is provided within a surface of each second electrode layer 12. Here, the insulating regions 11a and the insulating regions 12a are located in different positions from each other within the respective electrode layers.

The vertical interconnections 13 and 14 are micro interconnections having diameters of about 30 µm, for example, and desirably of equal to or less than 20 µm. The vertical interconnections 13 and 14 are not necessarily and strictly vertical to the respective multilayered surfaces. The vertical interconnection 13 is provided so as to penetrate the PZT layers 10 and the first electrode layers 11 and pass through the insulating regions 12a within the second electrode layers 12. Further, the vertical interconnection 14 is provided so as to penetrate the PZT layers 10 and the second electrode layers 12 and pass through the insulating regions 11a within the first electrode layers 11. By thus locating the vertical interconnections 13 and 14, the plural first electrode layers 11 are connected in parallel by the vertical interconnection 13 and insulated from the vertical interconnection 14. On the other hand, the plural the second electrode layers 12 are connected in parallel by the vertical interconnection 14 and insulated from the vertical interconnection 13.

Here, the areas of the insulating regions 11a and 12a are made small in a range where the vertical interconnections 13 and 14 may have no contact with the electrode portions around the insulating regions 11a and 12a. For example, the diameters of the insulating regions 11a and 12a are desirably made equal to or less than twice the diameters of the vertical interconnections 13 and 14.

Figure 2A:
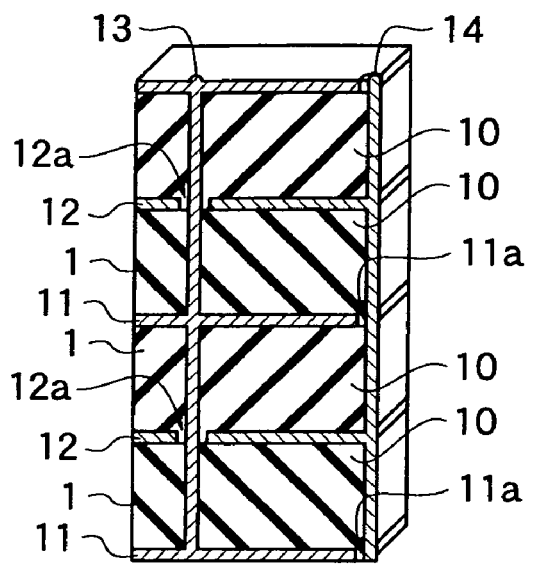
FIGS. 2A and 2B show modified examples of the multilayered structure as shown in FIGS. 1A and 1B.
Figure 2B:
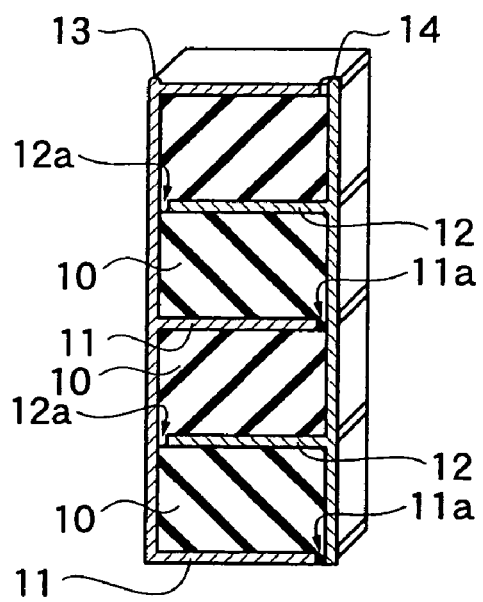

Further, although the vertical interconnections 13 and 14 are located inside the multilayered structure 1 in FIGS. 1A and 1B, their location is not limited to that in the present invention. For example, like a multilayered structure 2 as shown in FIG. 2A, any one of the vertical interconnections 13 and 14 may be located at an end of the multilayered structure 1. Alternatively, like a multilayered structure 3 as shown in FIG. 2B, both of the vertical interconnections 13 and 14 may be located at ends of the multilayered structure 1.

Next, a method of manufacturing the multilayered structure according to the first embodiment of the present invention will be described by referring to FIGS. 3 to 8C. In the embodiment, an arrayed multilayered structure is fabricated in which plural multilayered structures 1 as shown in FIGS. 1A and 1B are located. By the way, a single piece of multilayered structure can be fabricated by the same manufacturing method.

FIG. 3 is a flowchart showing the method of manufacturing the multilayered structure according to the embodiment.

Figure 4A:
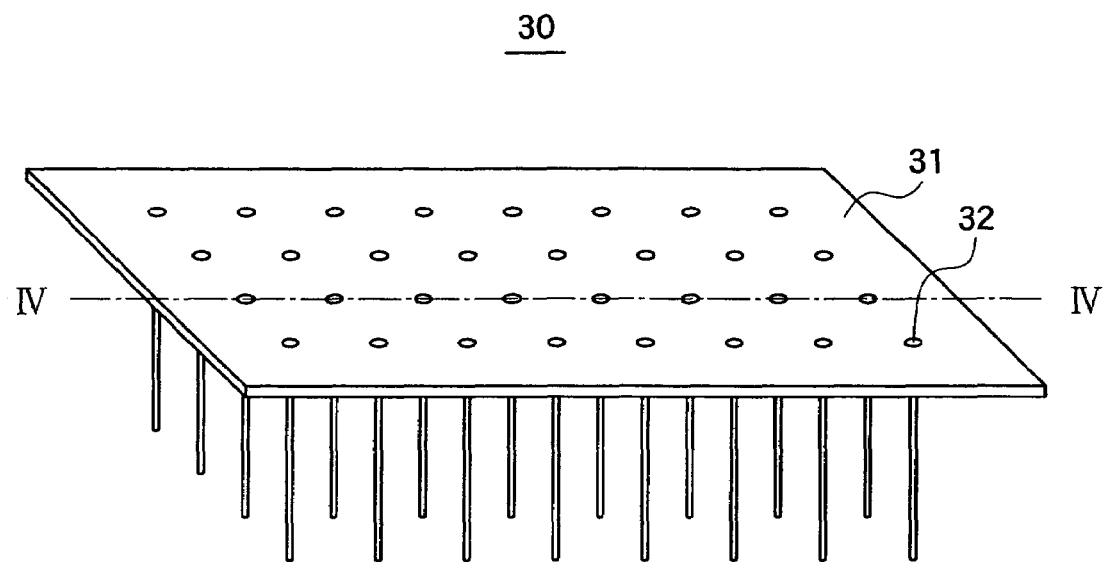
FIG. 4A is a perspective view showing a substrate having pins.
Figure 4B:
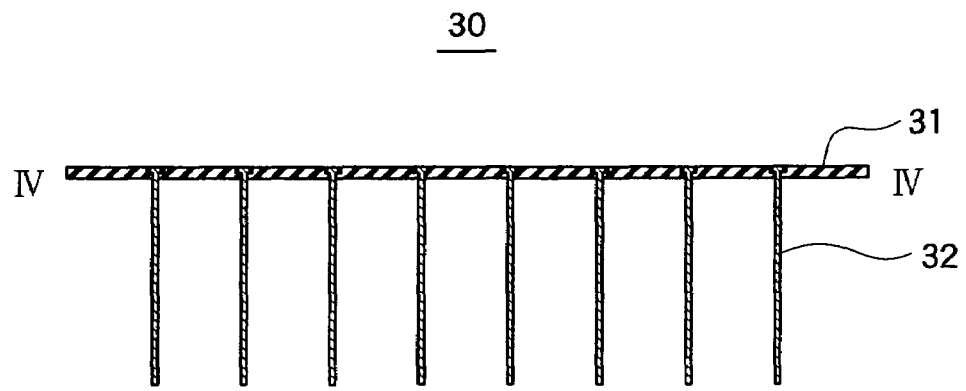
FIG. 4B is a sectional view along IV—IV plane in FIG. 4A.

First, at step S10, as shown in FIG. 4A, a substrate having pins (pin substrate) 30 is prepared. That is, plural holes are formed in a substrate 31 in a predetermined arrangement, and plural pins 32 are located in the holes. As a material of the substrate 31, for example, glass, machinable ceramic such as Macor (registered trademark), SUS (special use steel) or the like is used. Further, a material of the pins 32 is required to have a hardness of the degree that does not deform when an aerosol is sprayed thereon in the film forming process according to the AD method, which will be described later. As such a material, a hard material such as glass and ceramic, or a metal such as copper (Cu) and SUS can be cited. In the embodiment, metal pins of about 0.05 mm in a diameter are used. As shown in FIG. 4B, such plural pins 32 are arranged so as to penetrate the substrate 31. By the way, the pins are located after counterbores are provided in order to make the back surface of the pin substrate flat in FIG. 4B, however, the heads of the pins may be protruded from the back surface of the pin substrate without providing the counterbores.

Figure 5:
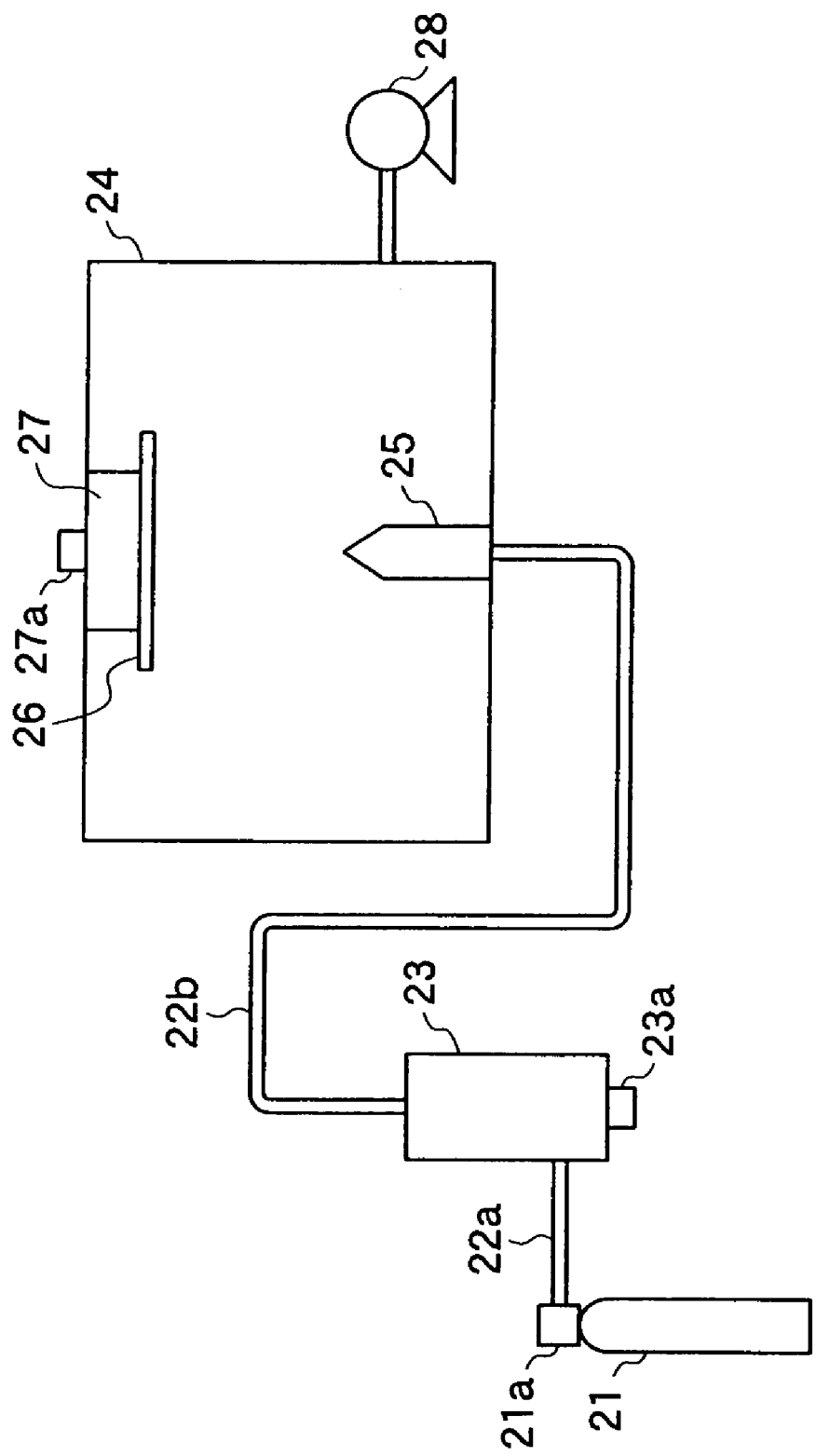
FIG. 5 is a schematic diagram showing a film forming device according to the AD method.

Then, at step S11, the PZT layers are formed on the pin substrate 30 by using a film forming device as shown in FIG. 5. In the embodiment, the aerosol deposition (AD) method is used when the PZT layers are formed.

FIG. 5 is a schematic diagram showing the film forming device according to the AD method. The film forming device includes a compressed gas cylinder 21, carrier pipes 22a and 22b, an aerosol generating part 23, a film forming chamber 24 in which film formation is performed, a nozzle 25 disposed in the film forming chamber 24, a substrate holder 27, and an exhaust pump 28.

The compressed gas cylinder 21 is filled with nitrogen ($N_2$) to be used as a carrier gas. Further, a pressure regulating part 21a for regulating the supplied amount of the carrier gas is provided to the compressed gas cylinder 21. As the carrier gas, not only nitrogen, but also oxygen ($O_2$), helium (He), argon (Ar) or dry air may be used.

The aerosol generating part 23 is a container for accommodating a micro powder of a raw material as a film forming material. By introducing the carrier gas via the carrier pipe 22a into the aerosol generating part 23, the raw material powder is blown up to generate an aerosol.

Further, a container driving part 23a for providing minute vibration or relatively slow motion to the aerosol generating part 23 is provided to the aerosol generating part 23. Here, the raw material powder (primary particles) located in the aerosol generating part 23 is coupled by the electrostatic force, Van der Waals force, or the like as time passes and form agglomerated particles. Among them, giant agglomerated particles in several micrometers to several millimeters have large masses and stay at the bottom of the container. If they stay near the exit of the carrier gas (near the exit of the carrier pipe 22a), it becomes impossible to blowup the primary particles by the carrier gas. Accordingly, in order to prevent the agglomerated particles from staying at one place, the container driving part 23a provides vibration or the like to the aerosol generating part 23 and agitates the powder located therein.

The nozzle 25 sprays the aerosol supplied from the aerosol generating part 23 via the carrier pipe 22b toward a substrate 26 at high speed. The nozzle 25 has an opening having a length of about 5 mm and a width of about 0.5 mm, for example.

The substrate holder 27 holds the substrate 26. Further, the substrate holder 27 is provided with a substrate holder driving part 27a for moving the substrate 26 in a three-dimensional manner. Thereby, the relative position and the relative speed between the nozzle 25 and the substrate 26 are controlled.

The exhaust pump 28 exhausts air from inside of the film forming chamber 24 and holds the inside at a predetermined degree of vacuum.

Figure 6A:
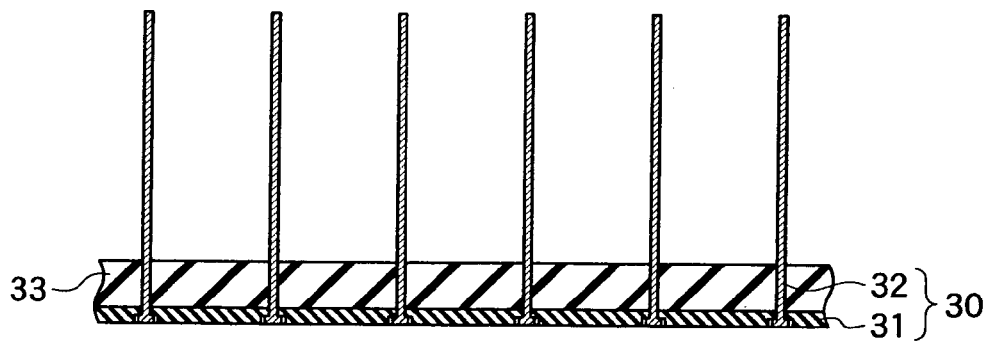
FIGS. 6A to 6C are diagrams for explanation of the method of manufacturing the multilayered structure according to the first embodiment of the present invention.

By using such a film forming device, a PZT monocrystal powder having an average particle diameter of 0.3 μm as a raw material, for example, is provided in the aerosol generating part 23, and the pin substrate 30 is placed on the substrate holder 27 and film formation is performed. Thereby, as shown in FIG. 6A, a PZT layer 33 is formed.

Figure 6B:
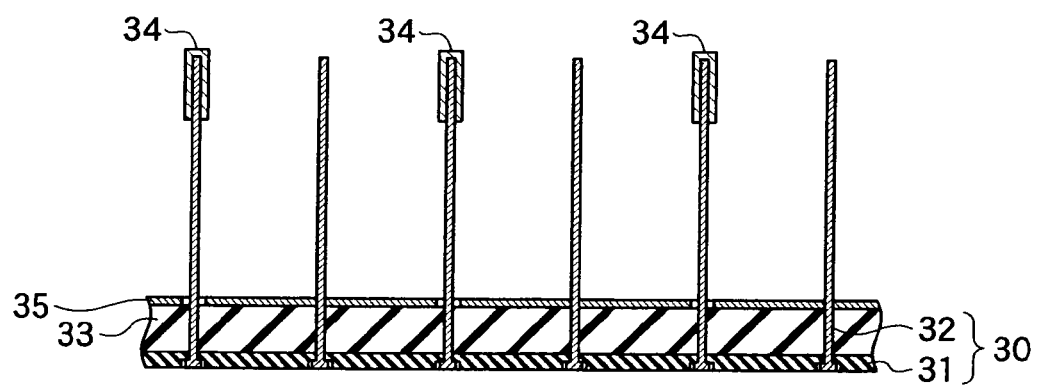

Then, at step S12, as shown in FIG. 6B, masks 34 are arranged in first regions, and a first electrode layer 35 is formed on the PZT layer 33 in accordance with the AD method. The masks 34 are cover pins for covering around the respective pins, for example, and arranged so as to cover the insulating regions 11a as shown in FIG. 1B. Further, as a conducting material, for example, a metal such as nickel (Ni), platinum (Pt), palladium silver (Ag—Pd) or an alloy is used. Thereby, the first electrode layer 35 is formed in regions other than the insulating regions 11a. By the way, as the film forming method, not only the AD method, but also the vacuum deposition method, sputtering method, or the like may be used.

Figure 6C:
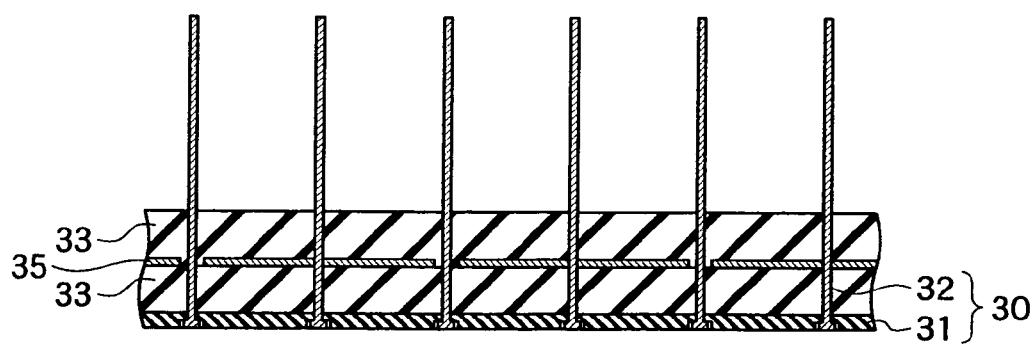

At step S13, after the masks 34 are removed, as shown in FIG. 6C, a PZT layer 33 is formed on the electrode layer 35 using the AD method.

Figure 7A:
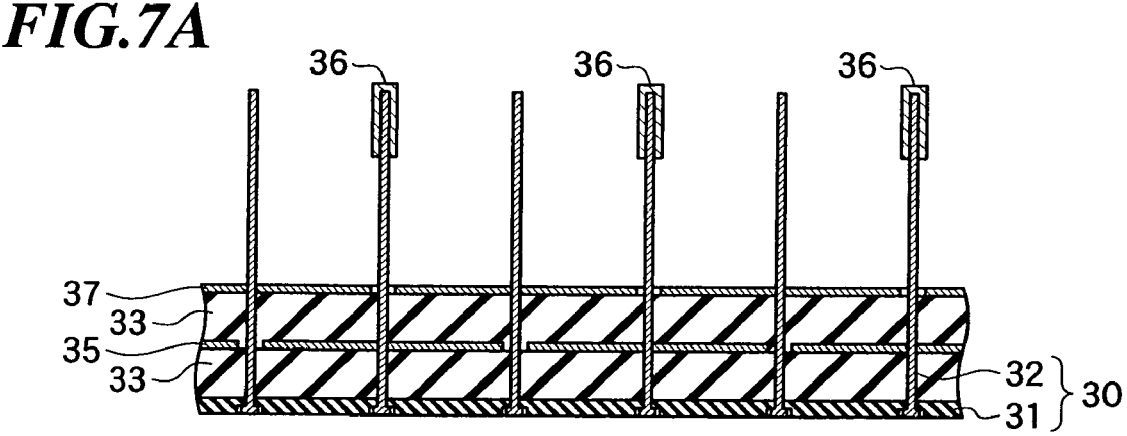
FIGS. 7A to 7C are diagrams for explanation of the method of manufacturing the multilayered structure according to the first embodiment of the present invention.

Then, at step S14, as shown in FIG. 7A, masks 36 are placed in second regions and a second electrode layer 37 is formed on the PZT layer 33 in accordance with the AD method. The masks 36 are cover pins for covering around the respective pins, for example, and arranged so as to cover the insulating regions 12a as shown in FIG. 1B.

Furthermore, at step S15, after the masks 36 are removed, a PZT layer 33 is formed on the second electrode layer 35 in accordance with the AD method. By repeating these steps S12 to S15, as shown in FIG. 7B, a multilayered structure 40 in which the plural PZT layers and electrode layers are alternately stacked is formed.

Figure 7B:
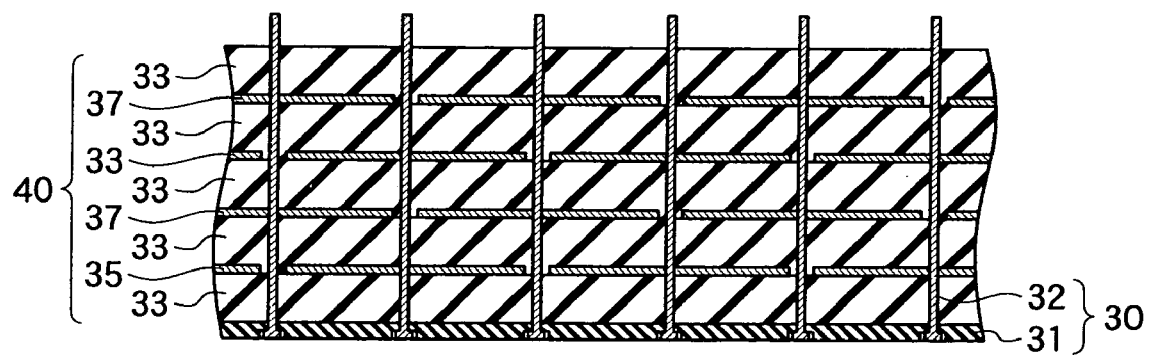
Figure 7C:
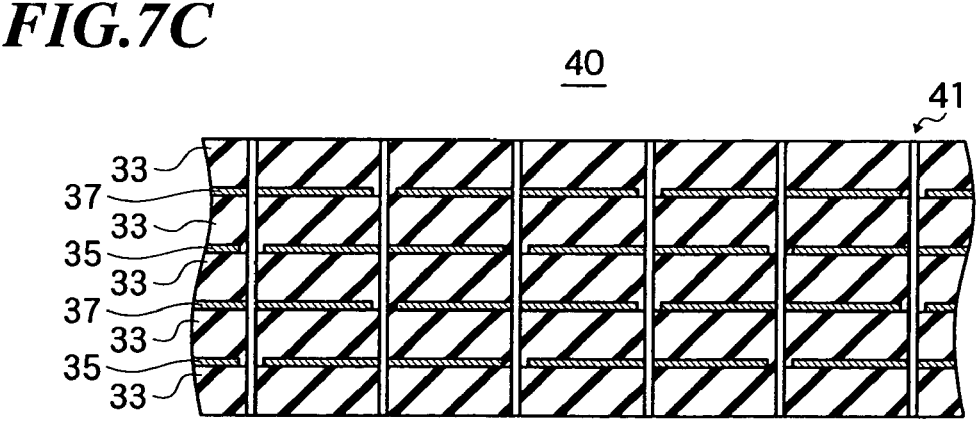

Then, at step S16, the pin substrate 30 is separated from a multilayered body 40 as shown in FIG. 7B. Thereby, as shown in FIG. 7C, the regions from which the pins 32 have been pulled out are left as holes 41 in the multilayered body 40. In the embodiment, since the PZT layers 33 are formed in accordance with the AD method, the pins 32 can be pulled out relatively easily from the multilayered body 40. The reason is as follows. In the AD method in which the raw material is deposited by the mechanochemical reaction when the raw material powder is crushed, the raw material powder strongly adheres to an object lying at right angles to the injection direction of the raw material powder (the lower layer in the embodiment), however, the adherence of the raw material is relatively weak to an object lying at other angles (e.g., the side surface of the pin) because the kinetic energy of the raw material powder is relatively small and easy to be crushed.

Figure 8A:
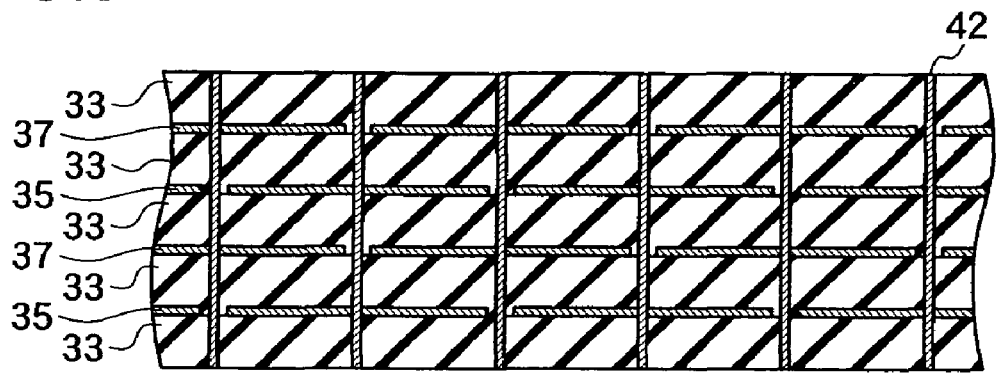
FIGS. 8A to 8C are diagrams for explanation of the method of manufacturing the multilayered structure according to the first embodiment of the present invention.

Then, at step S17, the holes 41 as shown in FIG. 7C are filled with a conducting material such as metal paste or carbon. Thereby, as shown in FIG. 8A, vertical interconnections 42 are formed. Alternatively, the vertical interconnections 42 may be formed by plating within the holes 41.

Figure 8B:
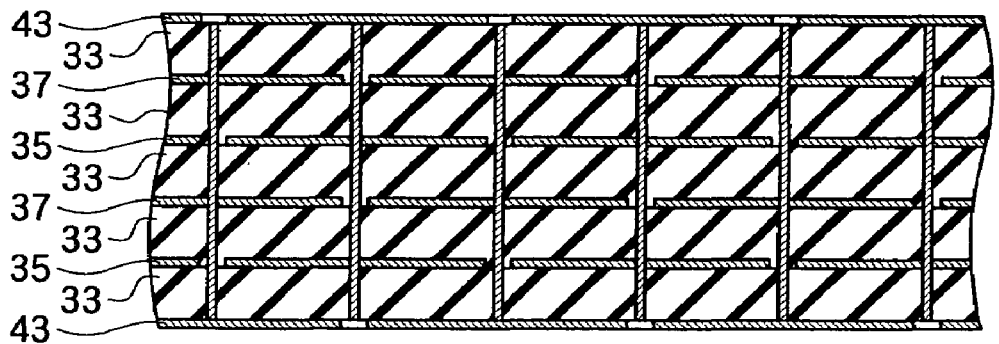

Then, at step S18, as shown in FIG. 8B, surface electrodes 43 are formed on the upper surface and lower surface of the multilayered body as shown in FIG. 8A.

Furthermore, at step S19, the multilayered body on which the surface electrodes have been formed is fixed to a supporting substrate 44, and cut with predetermined pitches by dicing or sandblasting machining. Thereby, as shown in FIG. 8C, an arrayed multilayered structure having the plural multilayered structures 1 arranged on the supporting substrate 44 is fabricated.

As described above, according to the embodiment, a micro multilayered structure in which plural piezoelectric material layers and electrode layers are alternately stacked and vertical interconnections are formed can be formed easily.

Figure 8C:
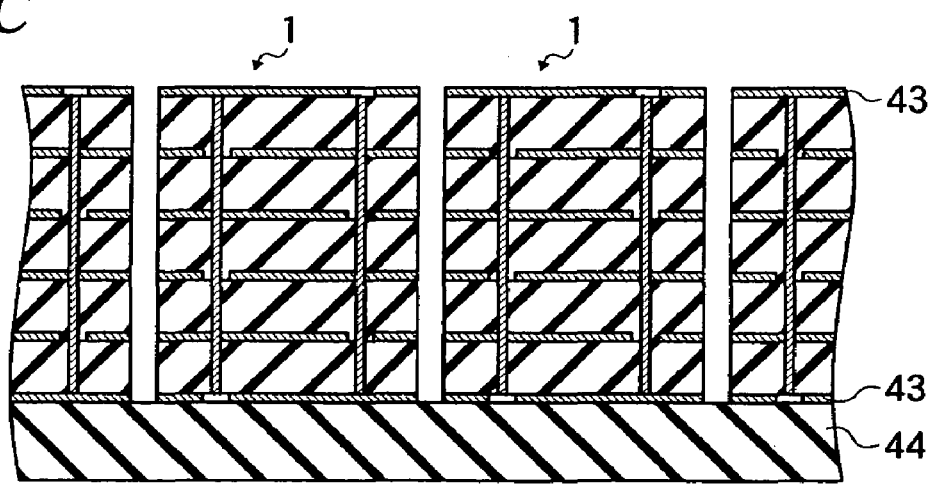
Figure 9:
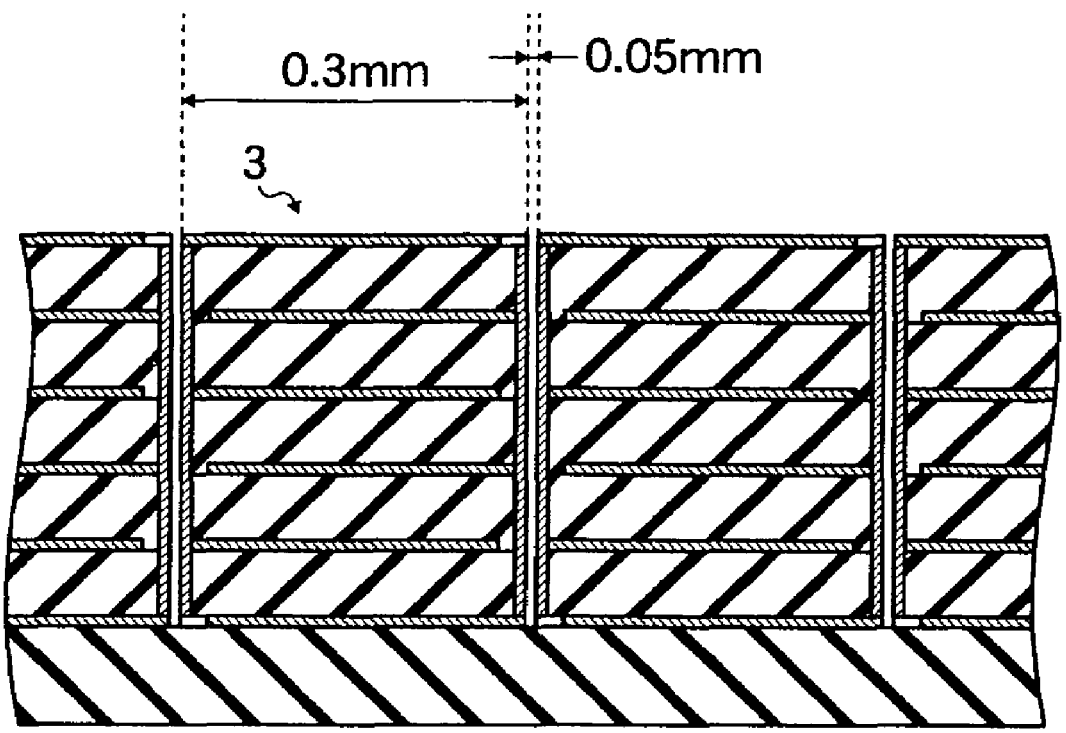
FIG. 9 is a diagram for explanation of a modified example of the method of manufacturing the multilayered structure according to the first embodiment of the present invention.

In the embodiment, as shown in FIG. 8C, two vertical interconnections are provided within the multilayered structure, however, those vertical interconnections may be provided on the side surfaces of the multilayered structure. For this purpose, at step S10 in FIG. 3, plural pins may be arranged in accordance with the element form of the multilayered structures to be fabricated. For example, as shown in FIG. 9, in the case where an arrayed multilayered structure having multilayered structures of 0.3 mm in width located at intervals of 0.05 mm is fabricated, pairs of pins spaced at 0.05 mm are arranged at intervals of 0.3 mm. Then, when the multilayered body is divided, it may be cut between the pairs of pins by using a dicing saw of 0.05 mm or less in width. In this case, the areas of the insulating regions provided around the vertical interconnections can be made smaller. Alternatively, like the multilayered structure 2 as shown in FIG. 2A, the positions of the pins arranged on the substrate, the cutting pitches or the like may be adjusted so that only one of the vertical interconnections maybe located on the side surface of the multilayered structure.

In the embodiment, the holes, in which the vertical interconnections are formed, are formed by pulling out the pins from the multilayered body 40. As in the embodiment, formation of the holes with a high aspect ratio (e.g., 1 mm in depth and 0.05 mm in diameter) has been difficult according to the conventional method using a drill. Further, it is conceivable to make the holes by the laser machining. However, in this case, not only a lot of time is required, but also the piezoelectric materials around the holes are affected by the heat generated at the time of laser machining. That is, there is a fear that the sizes of the crystal particles of the piezoelectric materials around the holes change, and the piezoelectric performance becomes deteriorated. On the other hand, according to the embodiment, minute holes can be formed easily without causing damage due to heat to the piezoelectric material.

Here, in the case where the pins 32 are difficult to be pulled out from the multilayered body 40 as shown in the FIG. 7B, the portions around the pins 32 may be coated with a material to which PZT is difficult to adhere. In the embodiment, because the PZT layers are formed in accordance with the AD method, it is desired that the portions are coated with a material having a cushion property such as a fluorocarbon resin, for example. Thereby, in the AD method, when the PZT powder injected from the nozzle impinges on the pins 32, the powder is bounced off by the coating material and the PZT powder hardly adheres to the pins 32.

Figure 10:
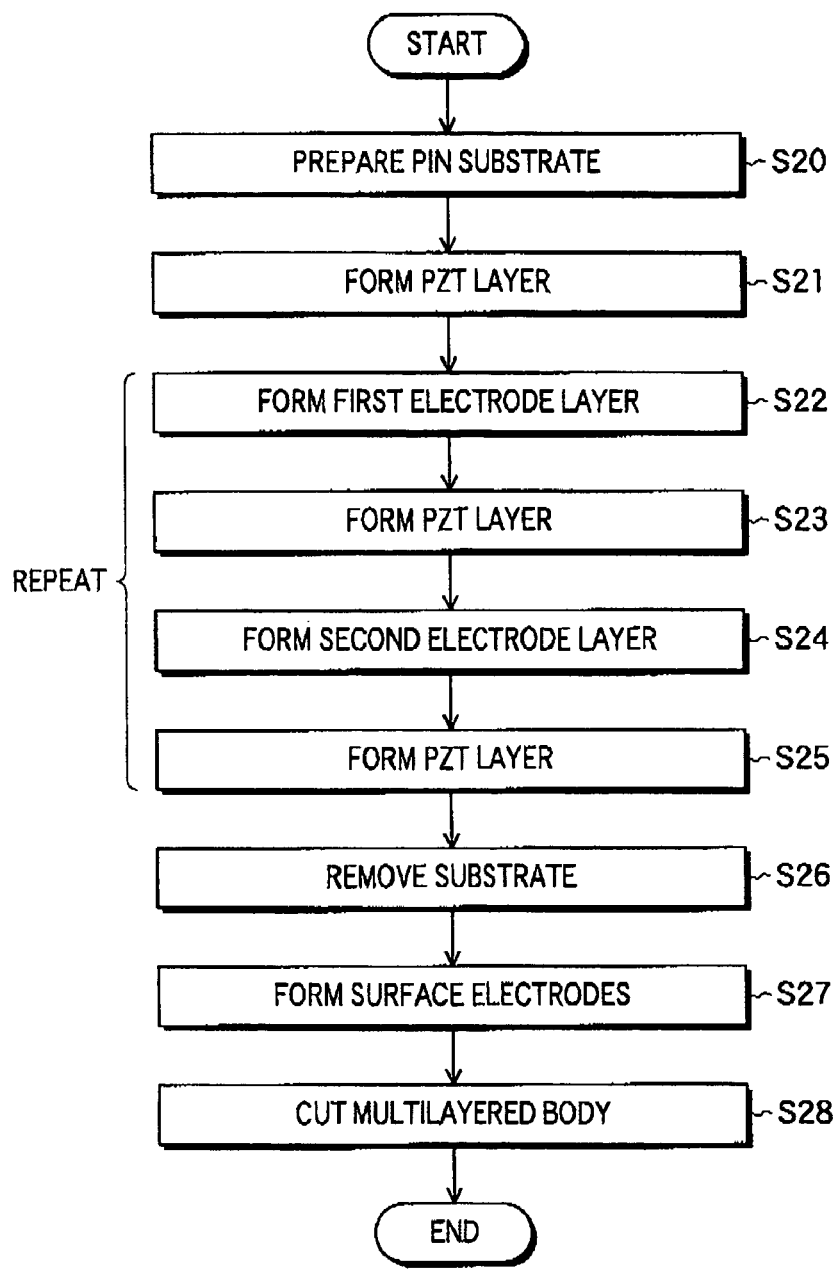
FIG. 10 is a flowchart showing a method of manufacturing a multilayered structure according to the second embodiment of the present invention.

Next, a method of manufacturing a multilayered structure according to the second embodiment will be described. FIG. 10 is a flowchart showing the method of manufacturing the multilayered structure according to the embodiment.

First, at step S20, as well as shown in FIGS. 4A and 4B, a pin substrate is prepared by arranging plural pins on a substrate. In the embodiment, as a material of the substrate, glass, ceramic, SUS, or the like can be used. Further, as a material of the pins, a conducting material such as a metal is used so that they can be used as electrodes later.

Then, at steps S21 to S24, as well as shown in FIGS. 6A to 7B, a multilayered body is formed on the pin substrate. That is, a PZT layer 33 is formed in accordance with the AD method at step S21, a first electrode layer 35 is formed by arranging masks 34 in the first insulating regions at step S22, a PZT layer 33 is formed in accordance with the AD method at step S23, a second electrode layer 37 is formed by arranging masks 36 in the second insulating regions at step S24, and a PZT layer 33 is formed in accordance with the AD method at step S25. The steps S22 to S25 are repeated at a predetermined number of times.

Figure 11A:
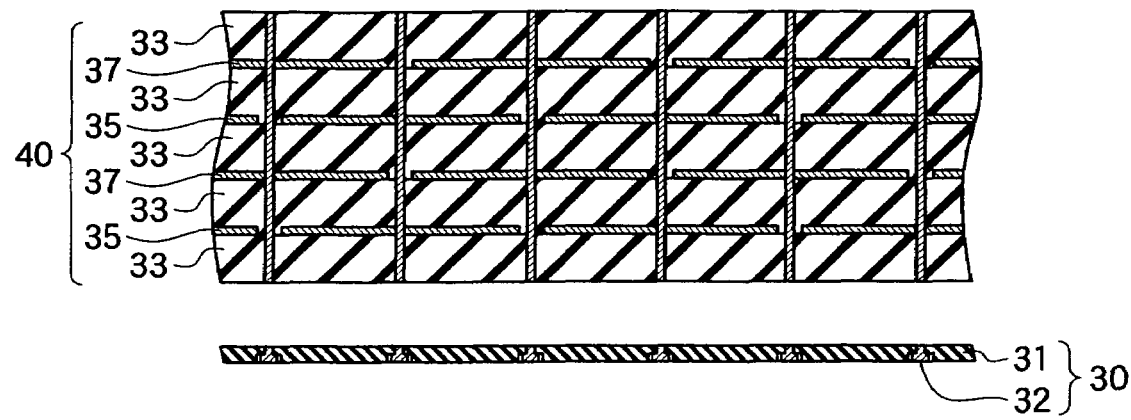
FIGS. 11A and 11B are diagrams for explanation of the method of manufacturing the multilayered structure according to the second embodiment of the present invention.

Then, at step S26, as shown in FIG. 11A, the formed multilayered body 40 and the pin substrate 30 are separated by cutting and the substrate 31 is removed with the inserted portions of the plural pins 32 left within the multilayered body 40. Alternatively, the substrate 31 may be removed by grinding or cutting.

Figure 11B:
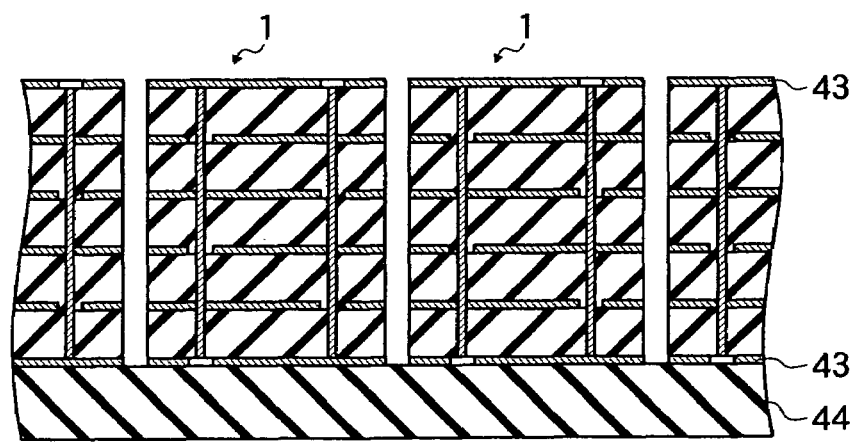

Then, at step S27, surface electrodes are formed on the upper surface and lower surface of the multilayered body as shown in FIG. 11A. Furthermore, at step S28, the multilayered body, on which the surface electrodes 43 have been formed, is fixed to a supporting substrate 44, and cut with predetermined pitches by dicing or sandblasting machining. Thereby, as shown in FIG. 11B, an arrayed multilayered structure having the plural multilayered structures 1 arranged on the supporting substrate 44 is fabricated.

According to the embodiment, since the pins that have been arranged on the substrate in advance are used as vertical interconnections, the manufacturing process can be simplified.

Here, when the vertical interconnections are formed, for example, if a method of forming holes in the multilayered body and filling them with paste is used, a binder is mixed in the vertical interconnections. Alternatively, if a method of plating the formed holes is used, a material first formed as a foundation (e.g., tin) remains within a material subsequently formed (e.g., copper). In either case, impurities are mixed in the vertical interconnections. Contrary, in the case of using the method according to the embodiment, the vertical interconnections are consisted only of the material that forms the pins. Therefore, which method has been used to form the vertical interconnections can be discriminated by analyzing the vertical interconnections.

Figure 12:
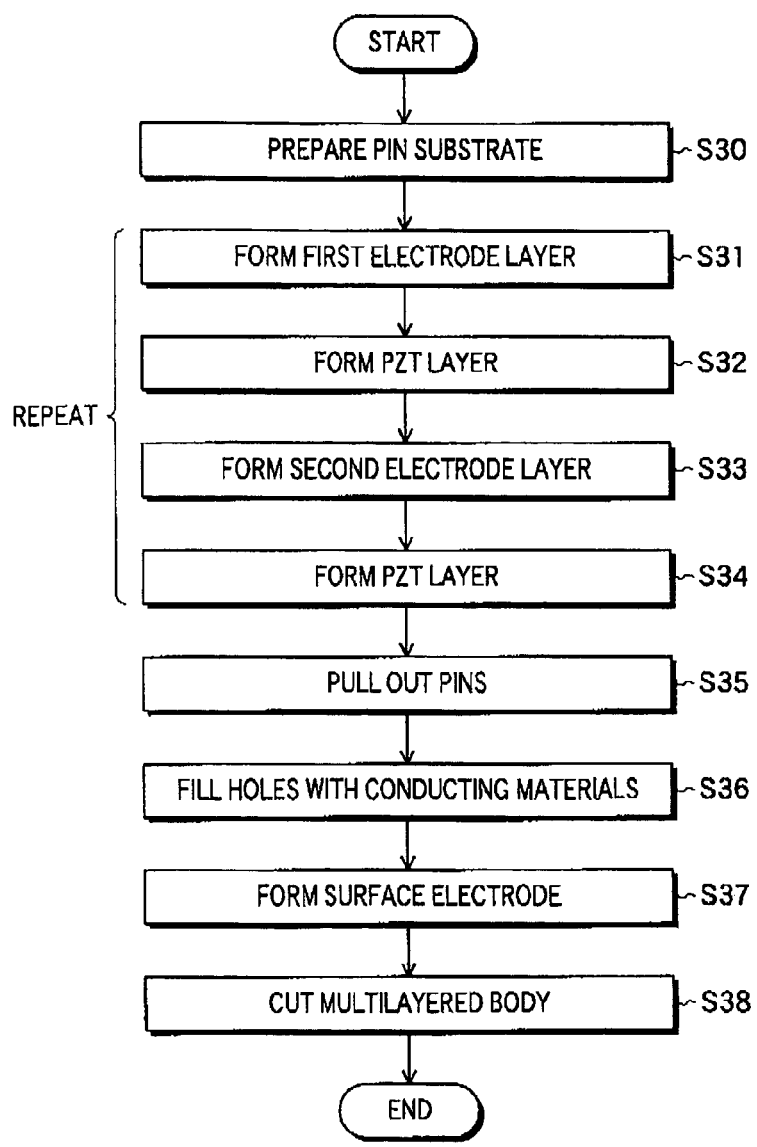
FIG. 12 is a flowchart showing a method of manufacturing a multilayered structure according to the third embodiment of the present invention.

Next, a method of manufacturing a multilayered structure according to the third embodiment will be described: FIG. 12 is a flowchart showing the method of manufacturing the multilayered structure according to the embodiment.

First, at step S30, as well as shown in FIG. 3, a pin substrate is prepared by arranging plural pins on a substrate. In the embodiment, such material is used as a material of the substrate that the fabricated multilayered structure including the substrate can be utilized as parts of a device. For example, in the case where the fabricated multilayered structure is used as an ultrasonic transducer included in an ultrasonic probe, glass, Macor (registered trademark), or the like is used as a material of the substrate so that the substrate may be utilized later as an acoustic matching layer or an acoustic matching material. Further, as a material of the pins, a material having a hardness of the degree that does not deform when an aerosol is sprayed thereon such as glass or SUS is used.

Figure 13A:
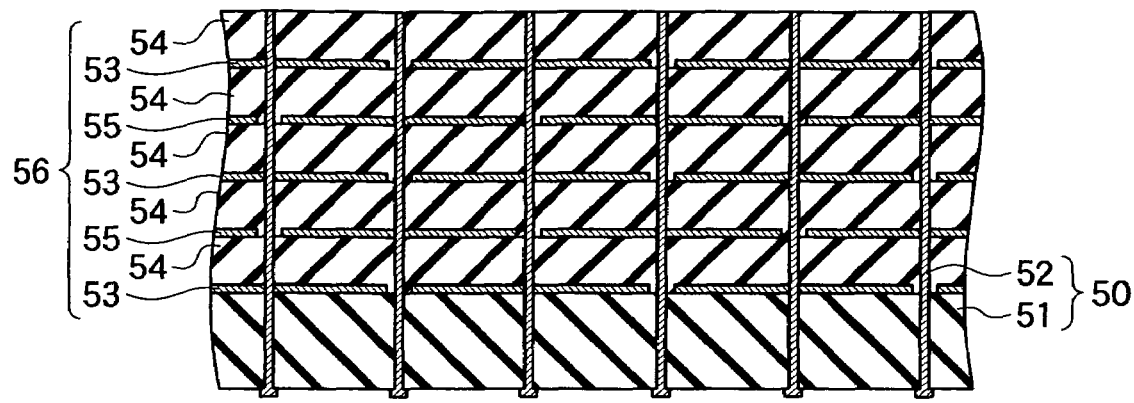
FIGS. 13A and 13B are diagrams for explanation of the method of manufacturing the multilayered structure according to the third embodiment of the present invention.

Then, at steps S31 to S34, as shown in FIG. 13A, a multilayered body is formed on a pin substrate 50 including a substrate 51 and pins 52. That is, a first electrode layer 53 is formed by arranging masks in the first insulating regions at step S31, a PZT layer 54 is formed in accordance with the AD method at step S32, a second electrode layer 55 is formed by arranging masks in the second insulating regions at step S33, and a PZT layer 54 is formed in accordance with the AD method at step S34. These steps S31 to S34 are repeated at a predetermined number of times.

Figure 13B:
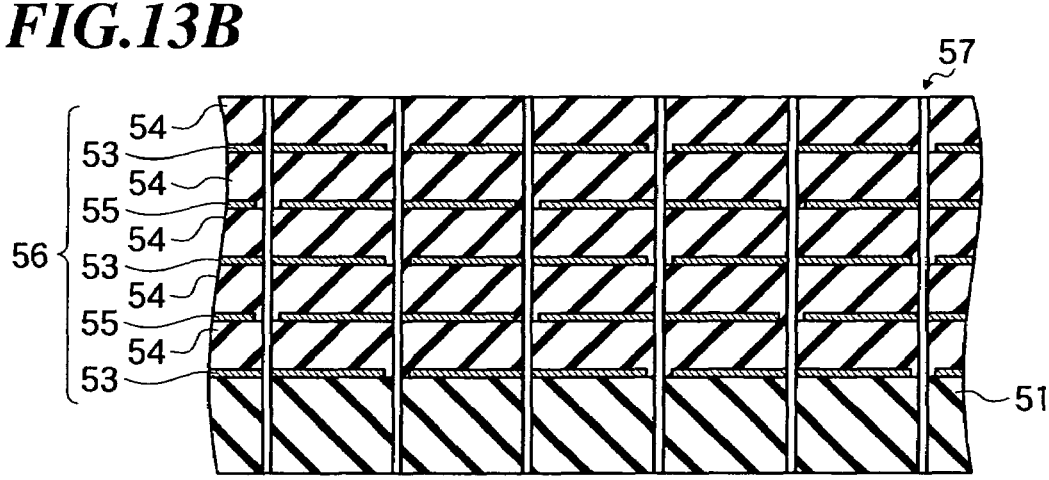

Then, at step S35, the plural pins 52 are pulled out from the substrate 51 and the multilayered body 56. Thereby, as shown in FIG. 13B, holes 57 are formed in the multilayered body 56.

Figure 14A:
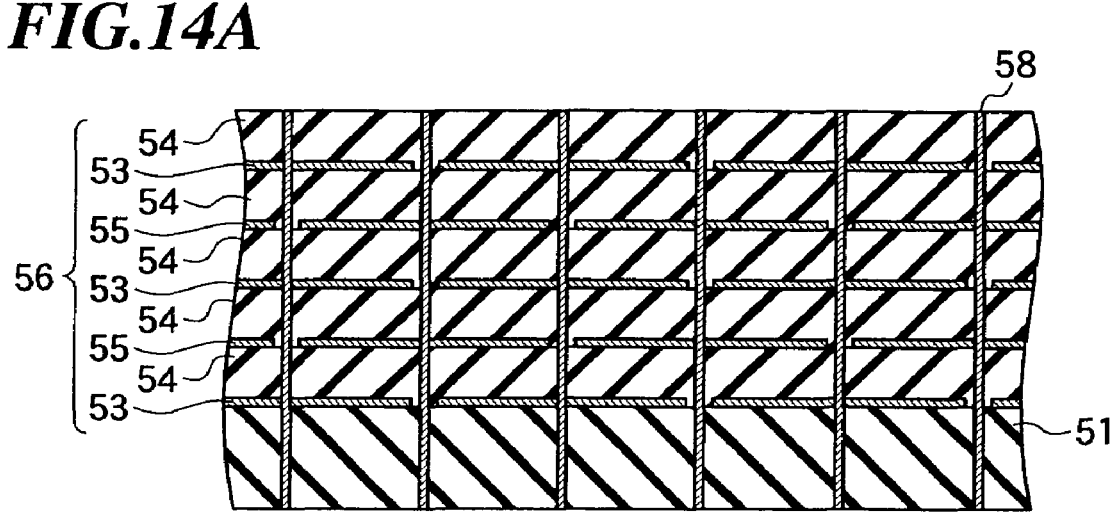
FIGS. 14A and 14B are diagrams for explanation of the method of manufacturing the multilayered structure according to the third embodiment of the present invention.

Then, at step S36, as shown in FIG. 14A, vertical interconnections 58 are formed by filling the holes 57 with a conducting material such as metal paste or carbon. Alternatively, the vertical interconnections 58 may be formed by plating within the holes 57.

Figure 14B:
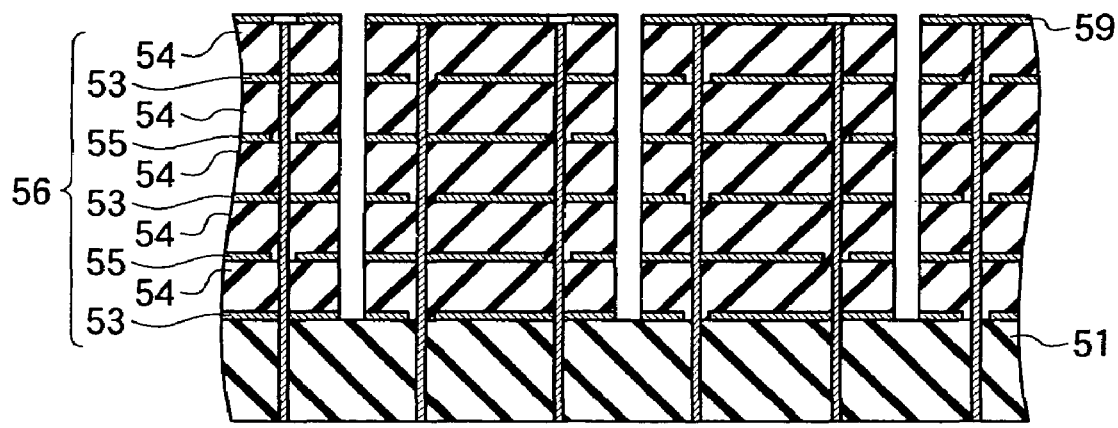

Furthermore, at step S37, a surface electrode 59 is formed on the upper surface of the multilayered body 56, and, at step S38, the layers upper than the substrate 51 of the multilayered body, on which the surface electrode is formed, are cut with predetermined pitches. Thereby, as shown in FIG. 14B, an arrayed multilayered structure having the plural multilayered structures 1 arranged on the supporting substrate 51 is fabricated.

According to the embodiment, since there is no need to separate the substrate when the multilayered structure is fabricated, the manufacturing process can be simplified.

Figure 15:
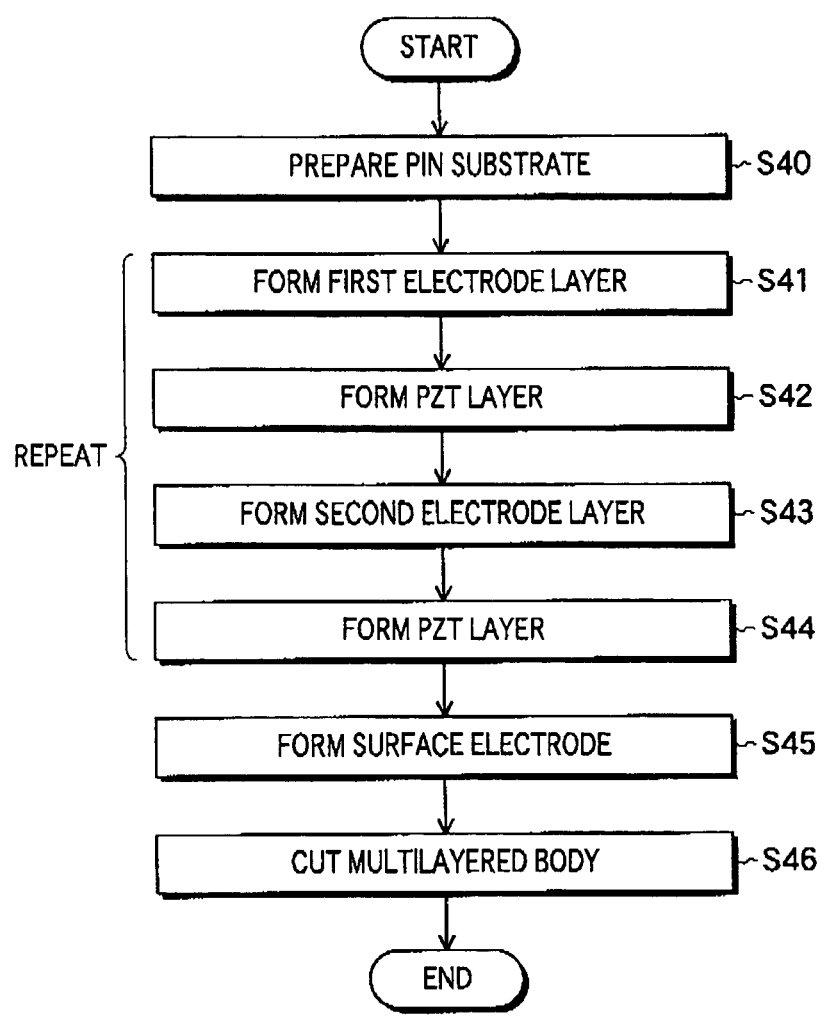
FIG. 15 is a flowchart showing a method of manufacturing a multilayered structure according to the fourth embodiment of the present invention.

Next, a method of manufacturing a multilayered structure according to the fourth embodiment will be described. FIG. 15 is a flowchart showing the method of manufacturing the multilayered structure according to the embodiment.

First, at step S40, as well as shown in FIG. 3, a pin substrate is prepared by arranging plural pins on a substrate. In the embodiment, as well as in the third embodiment, such material is used as a material of the substrate that the fabricated multilayered structure including the substrate can be utilized as parts of a device as it is. Further, as a material of the pins, a conducting material such as a metal is used so that they can be used later as electrodes.

Figure 16A:
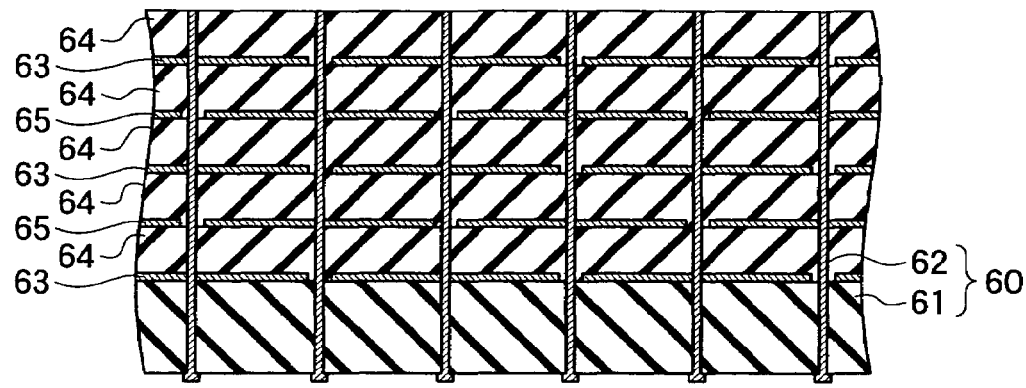
FIGS. 16A to 16C are diagrams for explanation of the method of manufacturing the multilayered structure according to the fourth embodiment of the present invention.

Then, at steps S41 to S44, as shown in FIG. 16A, a multilayered body is formed on a pin substrate 60 including a substrate 61 and pins 62. That is, a first electrode layer 63 is formed by arranging masks in the first insulating regions at step S41, a PZT layer 64 is formed in accordance with the AD method at step S42, a second electrode layer 65 is formed by arranging masks in the second insulating regions at step S43, and a PZT layer 64 is formed in accordance with the AD method at step S44. These steps S41 to S44 are repeated at a predetermined number of times.

Then, at step S45, a surface electrode 66 is formed on the surface of the multilayered body as shown in FIG. 16A, and, at step S46, the layers upper than the substrate 61 of the multilayered structure, on which the surface electrode 66 has been formed, are cut with predetermined pitches. Thereby, as shown in FIG. 16B, an arrayed multilayered structure having the plural multilayered structures 1 arranged on the substrate is fabricated.

Figure 16B:
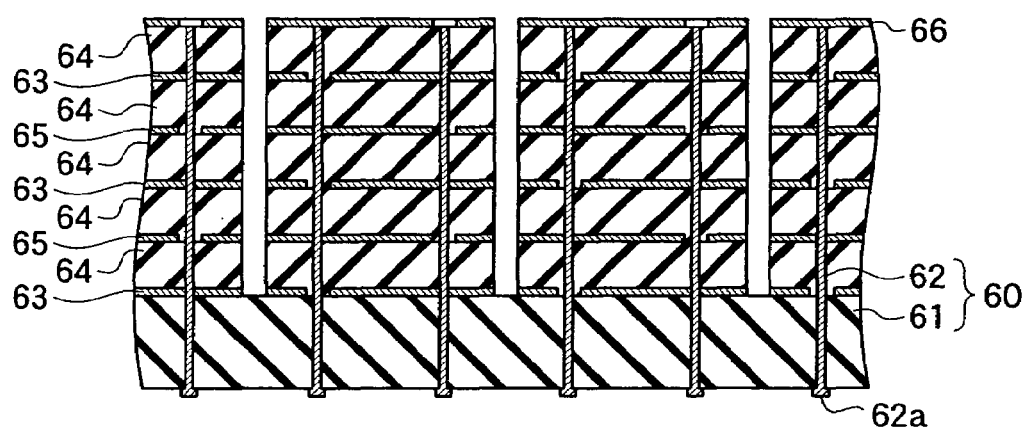
Figure 16C:
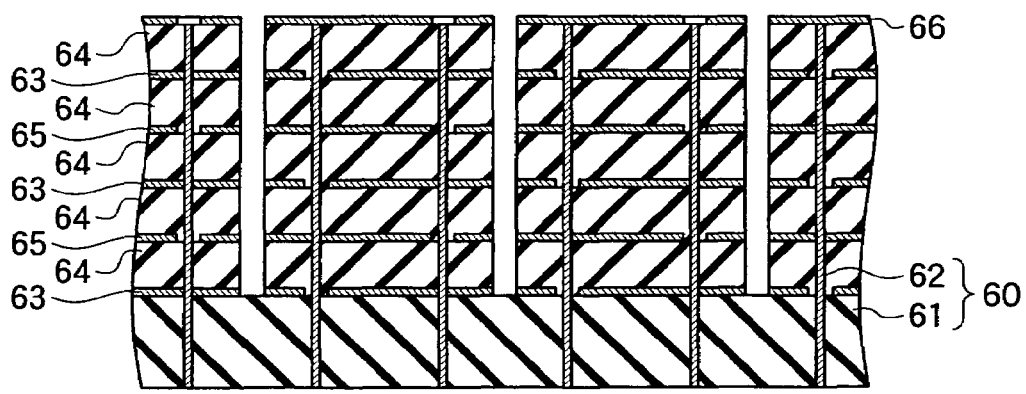

The arrayed multilayered structure as shown in FIG. 16B may be used as it is, or may be used with head portions 62a of the pins 62 cut as shown in FIG. 16C in accordance with the usage.

As described above, according to the embodiment since the substrate and pins, which have been used when the multilayered structure is fabricated, are not removed but used as the acoustic matching layer and electrodes, the manufacturing process can be simplified.

Figure 17:
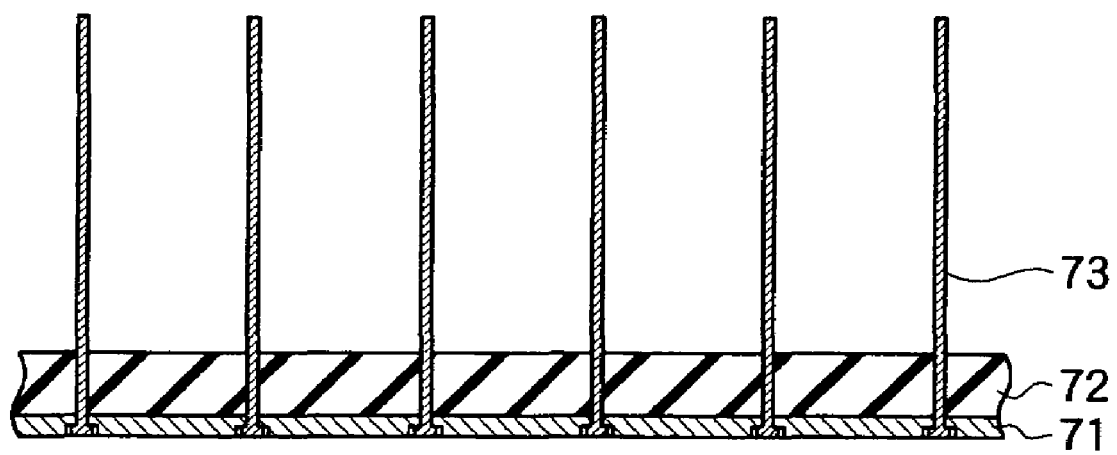
FIG. 17 is a diagram for explanation of a modified example of the method of manufacturing the multilayered structure according to the fourth embodiment of the present invention.

In the embodiment, the pin substrate is fabricated by arranging plural pins on a single-layer substrate. However, the pin substrate may be fabricated by using plural substrates. For example, as shown in FIG. 17, a pin substrate 70 having plural layers is fabricated by bonding a substrate 71 of SUS or the like for supporting and a substrate 72 of glass or the like for acoustic matching layer and arranging plural pins therein. After a multilayered body is formed on such a pin substrate 70, the substrate 71 for supporting and the substrate 72 for acoustic matching layer are separated by cutting. Thus, using two kinds of substrates, the substrate 72 for acoustic matching layer is protected by the substrate 71 for supporting during fabrication of the multilayered structure, and, after the fabrication of the multilayered structure, a desired acoustic matching function can be obtained by removing the substrate 71 for supporting that hinders acoustic matching.

In the above-described first to third embodiments of the present invention, the substrate or pins may be removed by separating the substrate from the multilayered body or cutting the pins. However, the substrate and pins may be removed by other methods. For example, the substrate and pins may be removed by using glass as a material of the substrate and pins and by dissolving the glass with hydrofluoric acid. Alternatively, the substrate and pins may be removed by using SUS as a material of the substrate and pins and by dissolving the SUS with ferric chloride solution.

Figure 18A:
FIGS. 18A and 18B show a modified example of a mask to be used in the methods of manufacturing the multilayered structure according to the first to fourth embodiments of the present invention.
Figure 18B:
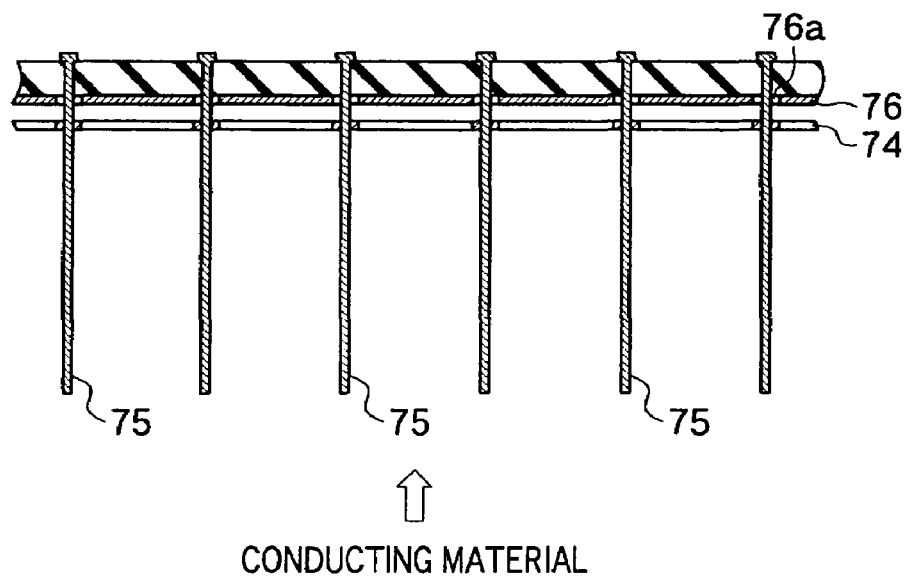

Further, in the first to fourth embodiments of the present invention, cover pins are used as masks when the electrode layers are formed. However, the masking method is not limited to such a method. FIG. 18A is a plan view showing an example of a mask that can be used in the first to fourth embodiments of the present invention, and FIG. 18B is a sectional view showing the state in which the electrode layer is being formed by using the mask as shown in FIG. 18A. For example, as shown in FIG. 18A, ring-shaped masks 74 may be used. When the electrode layer is formed, as shown in FIG. 18B, pins 75 are put through the ring portions of the masks 74 and a film of a conducting material is formed in a condition in which the masks are placed at the feet of the pins 75. Thereby, an electrode layer 76 provided with insulating regions 76a is formed. In the case where the mask regions are changed, the ring-shaped masks 74 may be once pulled from the pins 75, moved to the next mask regions, and then, placed at the feet of the pins 75 again. Thus, by making the masks closer to the regions in which films are formed, the accuracy of the insulating regions provided in the electrode layer can be made higher.

Figure 19A:
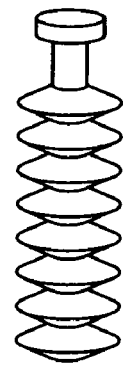
FIGS. 19A and 19B show another modified example of masks to be used in the method of manufacturing the multilayered structure according to the first to fourth embodiments of the present invention.
Figure 19B:
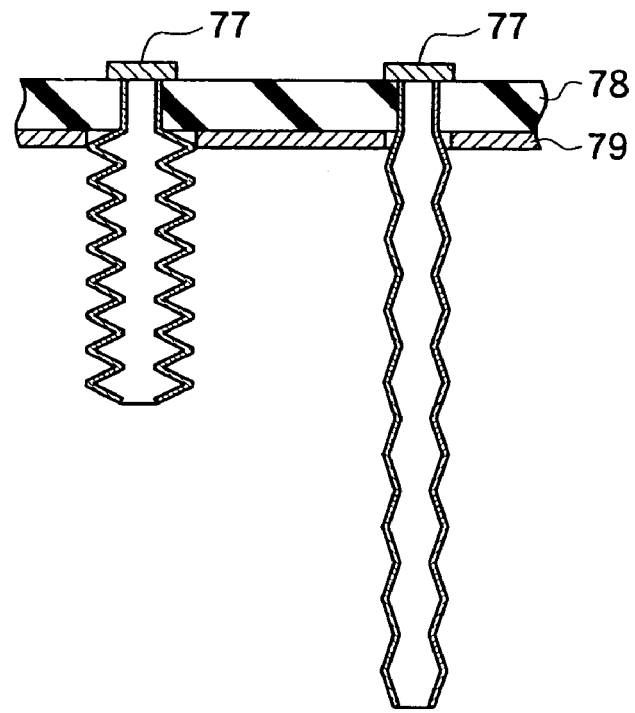

Further, FIGS. 19A and 19B show another example of masks that can be used in the first to fourth embodiments of the present invention. For example, the bellows portion of the bellows pin 77 as shown in FIG. 19A may be used as a mask. That is, as shown in FIG. 19B, a pin substrate is fabricated by forming holes in a substrate 78 in a predetermined arrangement and arranging the bellows pins 77 in the holes. When an electrode layer is formed, as shown in the left part of FIG. 19B, the bellows of the pins, around which insulating regions are to be provided, are pushed and expanded. On the other hand, the bellows of other pins are kept stretched. A film of a conducting material is formed in this condition, and thereby, an electrode layer 79 provided with insulating regions can be formed. By the way, when PZT layers are formed, bellows of all bellows pins 77 may be kept stretched.

Figure 20A:
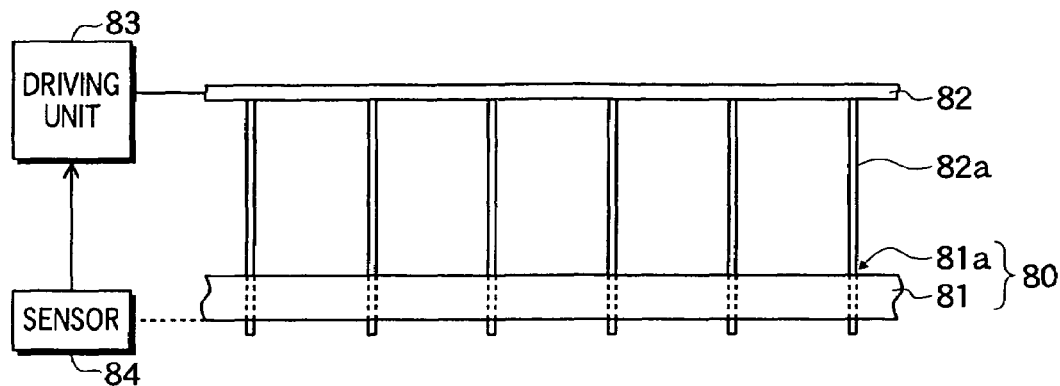
FIGS. 20A to 20C are diagrams for explanation of a method of manufacturing a multilayered structure according to the fifth embodiment of the present invention.
Figure 20B:
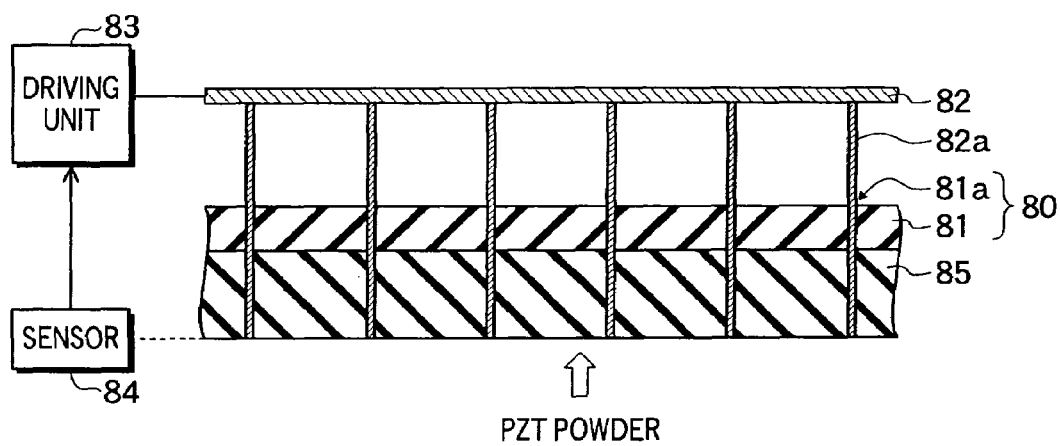
Figure 20C:
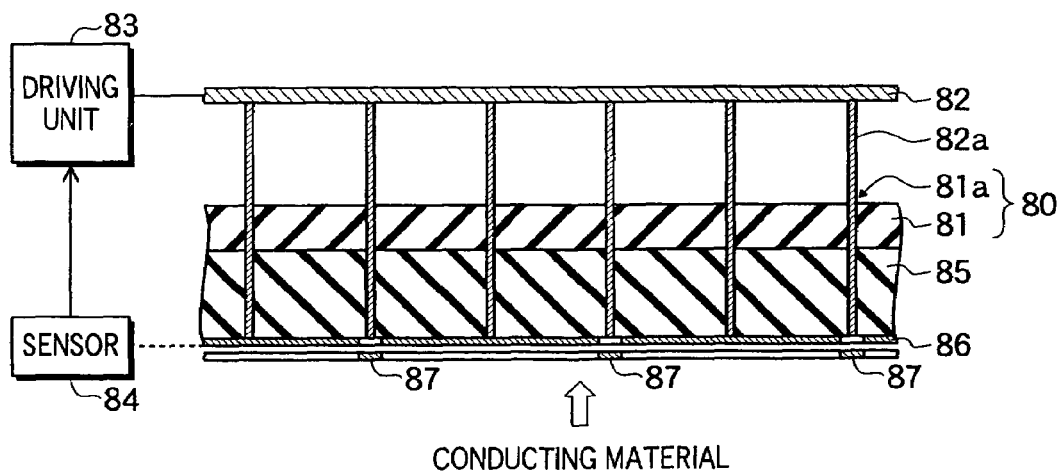

Next, a method of manufacturing a multilayered structure according to the fifth embodiment will be described. FIGS. 20A to 20C are schematic diagrams showing multilayered body manufacturing equipment made in accordance with the method of manufacturing the multilayered structure of the embodiment.

As shown in FIG. 20A, in the embodiment, when a multilayered structure is formed in which PZT layers and electrode layers are stacked, a movable pin substrate 80 is used. Movable pins 82 include plural pins 82a arranged in a predetermined arrangement and moving in conjunction with each other. In a substrate 81, plural holes 81a corresponding to the arrangement of the plural pins 82a are formed. The movable pin substrate 80 is formed by putting the plural pins 82a through these holes 81a, respectively.

A driving unit 83 is connected to the movable pins 82. The driving unit 83 includes a motor and a gear, for example, and moves the movable pins 82 in a predetermined orientation at a predetermined speed. Thereby, the positions of the substrate 81 and the movable pins 82 relatively change.

A sensor 84 is connected to the driving unit 83. As the sensor 84, for example, a position sensor using a laser can be used. The sensor 84 detects the thickness of the film formed on the movable pin substrate 84 by applying a laser thereto. The detection results of the sensor 84 are used in the driving unit 83 to control the moving speed of the movable pins 82.

As shown in FIG. 20B, in the case where a PZT layer is formed on the movable pin substrate 80 in accordance with the AD method, the sensor 84 monitors the thickness of the PZT layer formed by film formation. The driving unit 83 moves the movable pins by the same amount as the thickness of the layer based on the detection result of the sensor 84. Here, in the case where the film formation is performed toward the surface on which the pins protrude from the substrate by using the AD method, some parts of the region often become under the pins and the raw material powder is not uniformly sprayed onto the under layer. On the other hand, as shown in FIG. 20B, in the case where the protrusion lengths of the pins are adjusted in conjunction with the thickness of the formed layer, because the raw material powder is constantly sprayed toward a flat surface, the thickness of the PZT later can be made uniform.

Further, as shown in FIG. 20C, when an electrode layer 86 is formed, film formation is performed in accordance with the AD method by using masks 87. In this case, because a flat surface is masked, general masks can be used and mask regions can be changed easily. By the way, when the electrode layer 86 is formed, not only the AD method, but also other film forming method such as vacuum deposition method, sputtering method, or the like may be used.

Figure 21A:
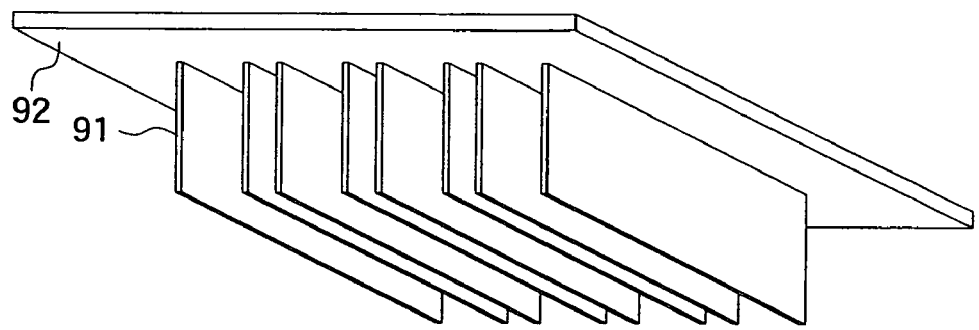
FIGS. 21A to 21C are diagrams for explanation of a modified example of the method of manufacturing the multilayered structure according to the fifth embodiment of the present invention.
Figure 21B:
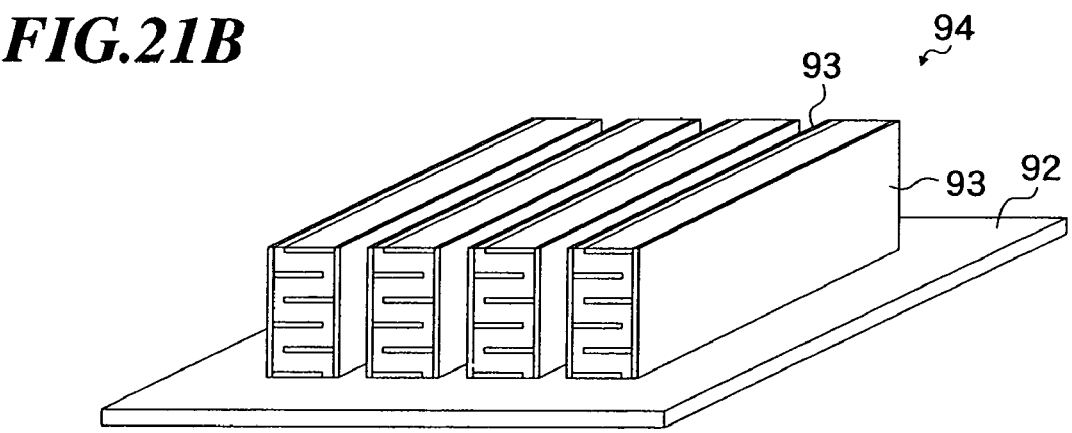
Figure 21C:
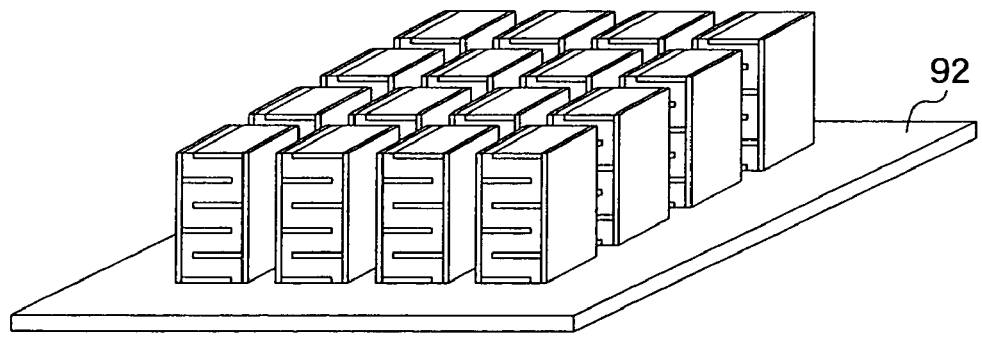

In the above-described first to fifth embodiments, the multilayered body is formed by forming a film by using the AD method on the substrate on which the plural pins have been arranged. However, other than that, film formation can be performed by arranging structures having various shapes (e.g., plate or column) on a substrate in advance. For example, as shown in FIG. 21A, plate-like structures 91 such as metal plates have been arranged on a substrate 92 in advance, and a multilayered structure is fabricated in the same way as described in the fourth embodiment of the present invention. Thereby, as shown in FIG. 21B, an arrayed multilayered structure in which plural multilayered structures 94 having side interconnections 93 are arranged in a one-dimensional manner can be fabricated. Furthermore, by cutting the multilayered structure 94 perpendicularly to the side interconnections 93, as shown in FIG. 21C, multilayered structures in a two-dimensional matrix form can be fabricated.

Figure 22:
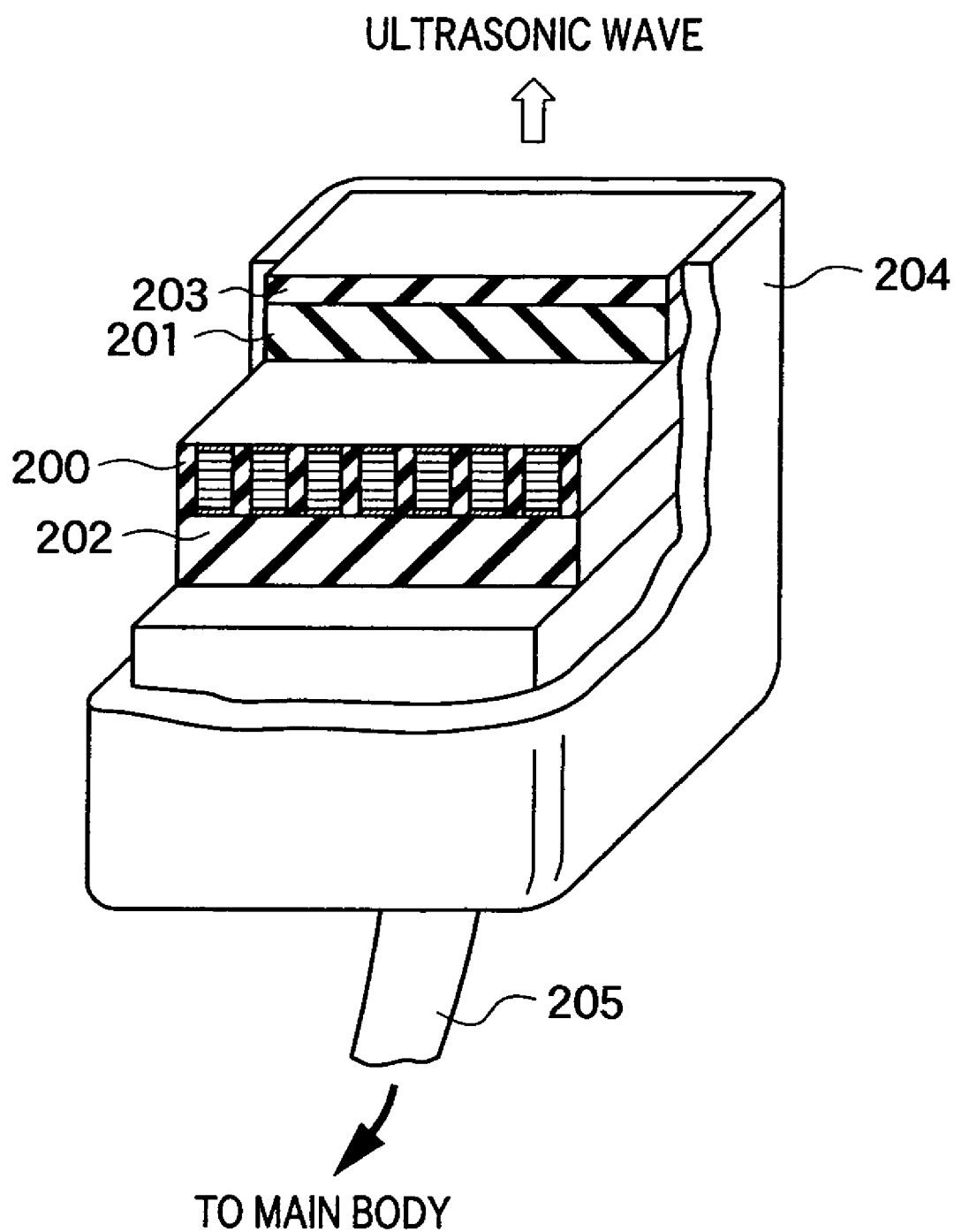
FIG. 22 is a partial sectional perspective view showing an ultrasonic probe including an arrayed multilayered structure fabricated by using the method of the multilayered structure according to the first to fifth embodiments of the present invention.
Figure 23A:
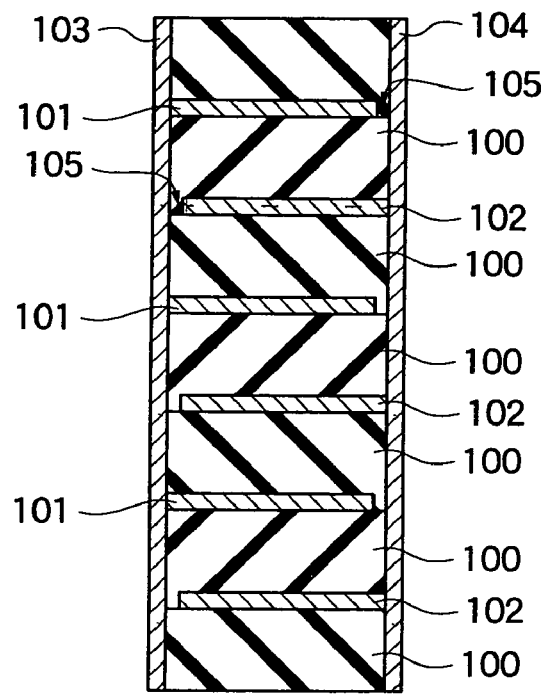
FIGS. 23A and 23B are diagrams for explanation of conventional multilayered structures.
Figure 23B:
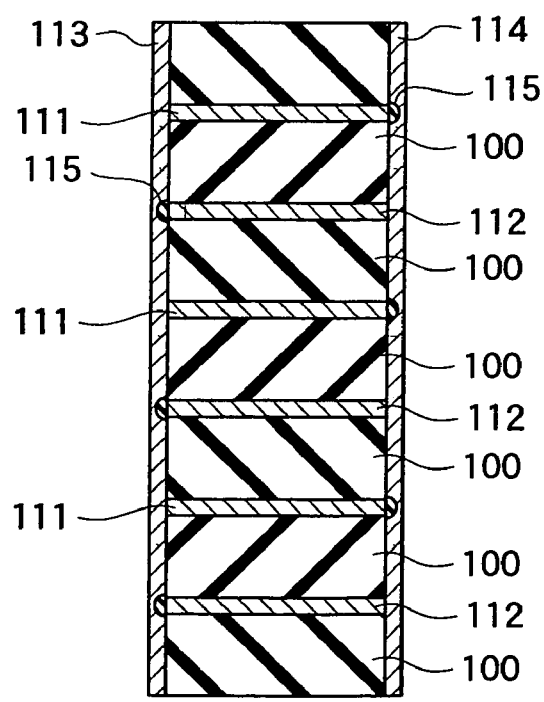

FIG. 22 is a partial sectional perspective view Showing an example in which the multilayered structure that has been fabricated in accordance with the method of the multilayered structure according to anyone of the first to fifth embodiments of the present invention is applied to an ultrasonic probe. The ultrasonic probe includes an ultrasonic transducer array 200, an acoustic matching layer 201, a backing layer 202, and an acoustic lens 203. These respective parts 200 to 203 are accommodated in a casing 204. Further, wirings drawn from the ultrasonic transducer array 200 are connected via a cable 205 to an ultrasonic imaging apparatus main body.

The ultrasonic transducer array 200 includes plural ultrasonic transducers for transmitting and receiving ultrasonic waves. Filling materials such as epoxy resin are arranged between these ultrasonic transducers. The acoustic matching layer 201 is formed by glass, ceramic, epoxy resin with metal powder, or the like that can transmit ultrasonic waves easily. The acoustic matching layer 201 eliminates a mismatch of the acoustic impedance between an object to be inspected as a living body and the ultrasonic transducer. Thereby, the ultrasonic wave transmitted from the ultrasonic transducer propagates efficiently within the object.

The backing layer 202 is formed by a material providing large acoustic attenuation such as a material in which powder of a metal, ferrite or PZT is mixed in epoxy resin or rubber. The backing layer 202 attenuates unwanted ultrasonic wave generated by the ultrasonic transducer array 200 rapidly. Furthermore, the acoustic lens 203 is formed by silicon rubber, for example. The acoustic lens 203 focuses an ultrasonic beam transmitted from the ultrasonic transducer array 200 and passed through the acoustic matching layer 201 at a predetermined depth.

When such an ultrasonic probe is fabricated, in the case where the method of manufacturing the multilayered structure according to the first, second, or fifth embodiment of the present invention is used, the ultrasonic transducer 200 is fabricated by filling space between the plural multilayered structures with filling materials, and the acoustic matching layer 201 is placed on one end surface of the ultrasonic transducer 200. On the other hand, in the case where the method of manufacturing the multilayered structure according to the third or fourth embodiment of the present invention is used, the ultrasonic transducer 200 and acoustic matching layer 201 are fabricated by filling space between the plural multilayered structures with filling materials in the arrayed multilayered structure fabricated by using glass or Macor (registered trademark) as the pin substrate. By the way, in this case, the acoustic matching layer having plural layers may be provided by bonding another acoustic matching layer to the substrate.

As described above, according to the present invention, a multilayered structure is formed by forming films of insulating materials in accordance with the injection deposition method over the substrate in which columnar structures have been formed in advance. Accordingly, the interconnections penetrating the insulating layers to be connected to the first or second electrode layers can be formed easily. Therefore, arraying of the multilayered structures, which has been conventionally difficult, can be realized with high reliability, and an ultrasonic transducer employing such a multilayered structure can be provided newly.

The invention claimed is:

1. A multilayered structure manufactured by using a substrate on which a plurality of columnar structures including a first group of columnar structures and a second group of columnar structures are arranged in a predetermined arrangement, said multilayered structure comprising:
   a first electrode layer formed by forming a film of a conducting material on one of said substrate and an insulating layer formed over said substrate except for portions around said first group of columnar structures;
   an insulating layer formed by spraying powder of an insulating material on said first electrode layer formed over said substrate to deposit the powder thereon;
   a second electrode layer formed by forming a film of a conducting material on said insulating layer except for portions around said second group of columnar structures; and
   a plurality of interconnections formed by filing, with a conducting material, a plurality of holes formed by removing said plurality of columnar structures from said substrate on which at least said first electrode layer, said insulating layer and said second electrode layer are formed.

2. A multilayered structure manufactured by using a substrate, said multilayered structure comprising:
   a plurality of electrodes formed by arranging a plurality of columnar structures including a first group of columnar structures and a second group of columnar structures formed of a conducting material on said substrate in a predetermined arrangement;
   a first electrode layer formed by forming a film of a conducting material on one of said substrate and an insulating layer formed over said substrate except for portions around said first group of columnar structures;
   an insulating layer formed by spraying powder of an insulating material on said first electrode layer formed over said substrate to deposit the powder thereon; and
   a second electrode layer formed by forming a film of a conducting material on said insulating layer except for portions around said second group of columnar structures.

3. An ultrasonic transducer manufactured by using a substrate on which a plurality of columnar structures including a first group of columnar structures and a second group of columnar structures are arranged in a predetermined arrangement, said ultrasonic transducer comprising:
   said substrate to be used as an acoustic matching layer;
   a first electrode layer formed by forming a film of a conducting material on said substrate except for portions around said first group of columnar structures;
   a piezoelectric material layer formed by spraying powder of a piezoelectric material on said first electrode layer formed over said substrate to deposit the powder thereon;
   a second electrode layer formed by forming a film of a conducting material on said piezoelectric material layer except for portions around said second group of columnar structures; and
   a plurality of interconnections formed by filing, with a conducting material, a plurality of holes formed by removing said plurality of columnar structures from said substrate on which at least said first electrode layer, said piezoelectric material layer and said second electrode layer are formed.

4. An ultrasonic transducer comprising:
   a substrate, on which a plurality of columnar structures including a first group of columnar structures and a second group of columnar structures are arranged in a predetermined arrangement, to be used as an acoustic matching layer;
   a first electrode layer formed by forming a film of a conducting material on said substrate except for portions around said first group of columnar structures;
   a piezoelectric material layer formed by spraying powder of a piezoelectric material on said first electrode layer formed over said substrate to deposit the powder thereon; and
   a second electrode layer formed by forming a film of a conducting material on said piezoelectric material layer except for portions around said second group of columnar structures.

5. A method of manufacturing a multilayered structure, said method comprising the steps of:
   arranging a plurality of columnar structures including a first group of columnar structures and a second group of columnar structures on a substrate in a predetermined arrangement;
   forming a first electrode layer by forming a film of a conducting material on one of said substrate and an insulating layer formed over said substrate except for portions around said first group of columnar structures;
   forming an insulating layer by spraying powder of an insulating material on said first electrode layer formed over said substrate to deposit the powder thereon; and
   forming a second electrode layer by forming a film of a conducting material on said insulating layer except for portions around said second group of columnar structures.

6. The method according to claim 5, further comprising the steps of:
   forming a plurality of holes in said multilayered structure by removing said plurality of columnar structures from said substrate on which at least said first electrode layer, said insulating layer and said second electrode layer are formed; and
   filing, with a conducting material, the plurality of holes formed in said multilayered structure.

7. The method according to claim 6, further comprising the step of removing said substrate from said multilayered structure.

8. The method according to claim 5, wherein said plurality of columnar structures are formed of a conducting material.

9. The method according to claim 8, further comprising the step of removing said substrate from said multilayered structure.

10. The method according to claim 5, further comprising the step of removing said substrate from said multilayered structure.

* * * * *